(12) United States Patent
Asturias Ortega et al.

(10) Patent No.: US 8,951,530 B2
(45) Date of Patent: Feb. 10, 2015

(54) HYPOALLERGENIC HYBRID PROTEINS OF MAJOR GROUP 1 AND 2 MITE ALLERGENS FOR USE IN THE TREATMENT OF ALLERGIES

(75) Inventors: Juan Andrés Asturias Ortega, Bilbao (ES); Iñaki Ibarrola Lopez De Davalillo, Bilbao (ES); Maria Carmen Arilla Rodriguez, Bilbao (ES); Alberto Martinez Garate, Bilbao (ES)

(73) Assignee: Bial Industrial Farmaceutica, S.A. (ES)

( * ) Notice: Subject to any disclaimer, the term of this patent is extended or adjusted under 35 U.S.C. 154(b) by 276 days.

(21) Appl. No.: 12/934,418

(22) PCT Filed: Mar. 24, 2009

(86) PCT No.: PCT/IB2009/005114
§ 371 (c)(1),
(2), (4) Date: Sep. 24, 2010

(87) PCT Pub. No.: WO2009/118642
PCT Pub. Date: Oct. 1, 2009

(65) Prior Publication Data
US 2011/0052640 A1    Mar. 3, 2011

(30) Foreign Application Priority Data
Mar. 25, 2008  (ES) .................................. 200800827

(51) Int. Cl.
| | | |
|---|---|---|
| *A61K 38/00* | (2006.01) | |
| *A61K 39/00* | (2006.01) | |
| *A61K 39/35* | (2006.01) | |
| *A61K 39/36* | (2006.01) | |
| *C07K 14/435* | (2006.01) | |

(52) U.S. Cl.
CPC ........... *A61K 39/35* (2013.01); *C07K 14/43531* (2013.01)
USPC .................. 424/185.1; 424/192.1; 424/275.1; 514/1.1

(58) Field of Classification Search
None
See application file for complete search history.

(56) References Cited

U.S. PATENT DOCUMENTS

| | | | |
|---|---|---|---|
| 5,433,948 A * | 7/1995 | Thomas et al. | 424/185.1 |
| 6,071,522 A * | 6/2000 | Thomas et al. | 424/275.1 |
| 7,288,256 B1 | 10/2007 | Garman et al. | |
| 2006/0263391 A1 | 11/2006 | Mothes et al. | |
| 2007/0065468 A1* | 3/2007 | Chua et al. | 424/275.1 |
| 2008/0286311 A1 | 11/2008 | Westritschnig et al. | |
| 2009/0148466 A1 | 6/2009 | Mothes et al. | |

FOREIGN PATENT DOCUMENTS

| | | |
|---|---|---|
| EP | 1219301 A1 | 7/2002 |
| EP | 1 440 979 A1 | 7/2004 |
| EP | 1674576 A1 | 6/2006 |
| EP | 1908777 A1 | 4/2008 |
| WO | WO 2004/005334 | 1/2004 |
| WO | WO 2005/085278 A1 | 9/2005 |
| WO | WO 2006/058359 A2 | 6/2006 |
| WO | 2007116089 A2 | 10/2007 |

OTHER PUBLICATIONS

Smith et al. 'Reduction in IgE binding to allergen variants generated by site-directed mutagenesis: Contribution of disulfide bonds to the antigenic structure of the major house dust mite allergen Der p 2.' Molec. Immunol. 33(4-5): 399-405, 1996.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Akcakya et al. "Local and Systemic Reactions During Immunotherapy with Adsorbed Extracts of House Dust Mite in Children" *Annals of Allergy, Asthma &Immunology*, vol. 85 (Oct. 2000) p. 317-321.
Akdis et al., "Mechanism of IL-10-Induced T Cell Inactivation in Allergic Inflammation and Normal Response to Allergens" *Int Arch Allergy Immunol* 124: 180-182 (2001).
de Blay at al., "Influence of Mite Exposure on Symptoms of Mite-Sensitive Patients with Asthma" *J. Allergy Clin Immunol* vol. 93 No. 1, Part 1, p. 136-138 (1994).
Ceska et al., "A New and Simple Radioimmunoassay Method for the Determination of IgE" *Immunochemistry* (1972) vol. 9, p. 1021-1030, Pergamon Press. Printed in Great Britain.
Chapman et al., "Epitope Mapping of Two Major Inhalant Allergens, *DER P I and DER F I*, From Mites of the Genus *Dermatophagoides*" *The Journal of Immunology* (1987) vol. 138, No. 5, p. 1479-1484, The American Association of Immunologists, Printed in U.S.A.
Chen et al., "Reduction of the in vivo Allergenicity of *Der p 2*, the Major House-Dust Mite Allergen, by Genetic Engineering" *Molecular Immunology* vol. 45 p. 2486-2498 (2008) Elsevier.
de Halleux et al., "Three Dimensional Structure and IgE-binding Properties of Mature Fully Active *Der p 1*, a Clinically Relevant Major Allergen" *J Allergy Clin Immunol* (Mar. 2006) p. 571-576.

(Continued)

*Primary Examiner* — Nora Rooney
(74) *Attorney, Agent, or Firm* — Lerner, David, Littenberg, Krumholz & Mentlik, LLP

(57) ABSTRACT

The present invention refers to recombinant ADN molecules coding to hybrids polypeptides of different allergens from *D. pteronyssinus* useful for the prevention and treatment of allergies, particularly allergies caused by mites. Specifically, the invention describes hybrid proteins composed of fragments of allergens Derp p 1 y Derp p 2 with hypoallergenic characteristics and maintain their immunogenic capacity, being particularly useful for the treatment of allergy. The invention also describes the production methods of these polypeptides in heterologous expression systems. Besides, the invention describes efficient purification methods of these hybrid proteins.

8 Claims, 14 Drawing Sheets

(56) References Cited

OTHER PUBLICATIONS

Hanahan "Studies on Transformation of *Escherichia coli* with Plasmids" *J. Mol. Biol.* (1983) vol. 166 p. 557-580, Academic Press inc. (London) Ltd.
Laemmli "Cleavage of Structural Proteins during the Assembly of the Head of Bacteriophage T4" *Nature* vol. 227, No. 5259 p. 680-685 (Aug. 15, 1970).
Meno et al., "The Cyrstal Structure of Recombinant *proDer p 1*, a Major House Dust Mite Proteolytic Allergen" *The Journal of Immunology* p. 3835-3845 (2005).
Meyer et al. "Comparison of the Levels of the Major Allergens *Der p I* and *Der p II* in Standardized Extracts of the House Dust Mite, *Dermatophagoides pteronyssinus*" *Clinical and Experimental Allergy* (1994) vol. 24, p. 1041-1048.
Mothes-Luksch et al., "Disruption of Allergenic Activity of the Major Grass Pollen Allergen Phl p 2 by Reassembly as a Mosaic Protein" *The Journal of Immunology* (2008) vol. 181, p. 4864-4873.
Moverare, R., "Immunological Mechanisms of Specific Immunotherapy with Pollen Vaccines: Implications for diagnostics and the Development of Improved Vaccination Strategies" *Expert Rev. Vaccines* 2(1) (2003) pp. 85-97.
O'Brien et al. "An Immunogenetic Analysis of the T-cell Recognition of the Major House Dust Mite Allergen *Der p 2*: Identification of high- and low-responder HLA-DQ Alleles and Localization of T-cell Epitopes" *Immunology* (1995) vol. 86 p. 176-182, Blackwell Science.
Roistrup et al., "Allergic Disease and Sensitization in Steiner School Children" *J Allergy Clin Immunol* (Jan. 2006) p. 59-66.
Sanz et al, "Allergen-induced Basophil Activation: CD63 Cell Expression Detected by Flow Cytometry in Patients Allergic to *Dermatophagoides pteronyssinus* and *Lolium perenne*" *Clinical and Experimental Allergy* (2001) vol. 31, p. 1007-1013, Blackwell Science.
Thomas et al, "Characterization and Immunobiology of House Dust Mite Allergens" *Int Arch Allergy Immunol* (2002) vol. 129 p. 1-18, S. Karger AG, Basel.
Towbin et al, "Electrophoretic Transfer of Proteins from Polyacrylamide Gels to Nitrocellulose Sheets: Procedure and some Applications" *Proc. Natl. Acad, Sci. USA* vol. 76, No. 9, p. 4350-4354 (Sep. 1979).
van der Zee et al., "Skin Tests and Histamine Release with $P_1$-depleted *Dermatophagoides pteronyssinus* body Extracts and Purified $P_1$." *J Allergy Clin Immunol* vol. 1988 vol. 81 No. 5, part 1, p. 884-896.
van Ree et al., "Possible Induction of Food Allergy During Mite Immunotherapy" *Allergy* (1996) vol. 51, p. 108-113, Munksgaard.
Wachholz et al., "Inhibition of Allergen-IgE Binding to B Cells by IgG Antibodies After Grass Pollen Immunotherapy" Mechanisms of Allergy, *J Allergy Clin Immunol* (Nov. 2003) vol. 112, p. 915-922.
Way et al, "Identification of a Region in Segment 1 of Gelsolin Critical for Actin Binding" *The Embo Journal* vol. 9, No. 12, p. 4103-4109 (1990).
Asturias et al., "*par j 1* and *par j 2*, the Major Allergens from *Parietaria judaica* Pollen Have Similar Immunoglobulin E Epitopes" *Clin Exp Allergy* vol. 33, No. 4 (Apr. 2003) p. 518-524.
Bannon et al., "Evaluation of Available IgE-binding Epitope Data and Its Utility in Bioinformatics" *Molecular Nutrition and Food Research* vol. 50, No. 7 (Jul. 2006) p. 638-644.
Colombo et al. "Identification of an Immunodominant IgE Epitope of the *Parietaria judaica* Major Allergen" *Journal of Immunology*, vol. 160, No. 6 (Mar. 15, 1998) p. 2780-2785.
Ferreira et al. "Genetic Engineering of Allergens: Future Therapeutic Products" *Int Arch Allergy Immunol* (2002) vol. 128, No. 3, p. 171-178.
Linhart et al. "Molecular Design of Allergy Vaccines" *Current Opinion in Immunology*, (Dec. 2005) vol. 17, No. 6, p. 646-655.
Registration of Allergen Preparations, Nordic Guidelines, Prepared by the Nordic Council on medicines in Cooperation with the Drug Regulatory Authorities in Denmark, Finland, Iceland, Norway, Sweden, 2d edition (Jan. 1989) 35 pages.
P.L. Bhalla et al., "Biotechnology-based allergy diagnoses and vaccination," Trends in Biotechnology, Jan. 28, 2008, pp. 153-161, vol. 26, No. 3, Elsevier Publications, Cambridge, GB, XP022487059.
M Wallner et al., "Allergy multivaccines created by DNA shuffling of tree pollen allergens," Journal of Allergy and Clinical Immunology, Jul. 29, 2007, pp. 374-380, vol. 120, No. 2, Mosby—Yearly Book, Inc., US, XP022199094.
K.W. Chen et al., "Reduction of the in vivo allergenicity of *Der p 2*, the major house-dust mite allergen, by genetic engineering," Molecular Immunology, Mar. 4, 2008, pp. 2486-2498, vol. 45, No. 9, Pergamon, GB, XP022540428.
R. Gonzalez-Rioja et al., "Genetically engineered hybrid proteins from *Parietaria judaica* pollen for allergen-specific immunotherapy," Journal of Allergy and Clinical Immunology, Aug. 31, 2007, pp. 602-609, Mosby—Yearly Book, Inc., US, XP022212638.
R. Crameri et al., Novel vaccines and adjuvants for allergen-specific immunotherapy, Current Opinion in Immunology, Dec. 1, 2006, pp. 761-768, Elsevier, Oxford, GB, XP025078999.
J. Holm et al., "Allergy vaccine engineering: Epitope modulation of recombinant Bet v 1 reduces IgE binding but retains protein folding pattern for induction of protective blocking-antibody responses," Journal of Immunology, Oct. 25, 2004, pp. 5258-5267, vol. 173, No. 8, XP009123652.
R. Mantyjarvi et al., "Lipocalins as allergens," Biochimica et Biophysica Acta—Protein Structure and Molecular Enzymologie, Oct. 18, 2000, pp. 308-317, vol. 1482, No. 1-2, Elsevier Science BV, Amsterdam, NL, XP004279083.
M. Akdis et al., "Mechanisms of allergen-specific immunotherapy," Journal of Allergy and Clinical Immunology, Apr. 5, 2007, pp. 780-789, vol. 119, No. 4, Mosby—Yearly Book, Inc., US, XP022020511.
G. Bannon et al., "Evaluation of available IgE-binding epitope data and its utility in bioinformatics," Molecular Nutrition & Food Research, Jul. 1, 2006, vol. 50, No. 7, Wiley—VCH Verlag, Weinheim, DE, XP002448731.

\* cited by examiner

```
cgtccatcatcgatcaaaacttttgaagaatacaaaaaagccttcaacaaaagttatgct
R  P  S  S  I  K  T  F  E  E  Y  K  K  A  F  N  K  S  Y  A
accttcgaagatgaagaagctgcccgtaaaaacttttttggaatcagtaaaatatgttcaa
T  F  E  D  E  E  A  A  R  K  N  F  L  E  S  V  K  Y  V  Q
tcaaacggaggtgccatcaaccatttgtccgatttgtcgttggatgaattcaaaaaccga
S  N  G  G  A  I  N  H  L  S  D  L  S  L  D  E  F  K  N  R
ttcttgatgagtgcagaagcttttgaacacctcaaaactcaattcgatttgaatgctgaa
F  L  M  S  A  E  A  F  E  H  L  K  T  Q  F  D  L  N  A  E
actaacgcctgcagtatcaatggaaatgctccagctgaaatcgatttgcgacaaatgcga
T  N  A  C  S  I  N  G  N  A  P  A  E  I  D  L  R  Q  M  R
actgtcactcccattcgtatgcaaggaggctgtggttcatgttgggcttttctctggtgtt
T  V  T  P  I  R  M  Q  G  G  C  G  S  C  W  A  F  S  G  V
gccgcaactgaatcagcttatttggcttaccgtaatcaatcattggatcttgctgaacaa
A  A  T  E  S  A  Y  L  A  Y  R  N  Q  S  L  D  L  A  E  Q
gaattagtcgattgtgcttcccaacacggttgtaatggtgataccattccacgtggtatt
E  L  V  D  C  A  S  Q  H  G  C  N  G  D  T  I  P  R  G  I
gaatacatccaacataatggtgtcgtccaagaaagctactatcgatacgttgcacgagaa
E  Y  I  Q  H  N  G  V  V  Q  E  S  Y  Y  R  Y  V  A  R  E
caatcatgccgacgaccaaatgcacaacgtttcggtatctcaaactattgccaaatttac
Q  S  C  R  R  P  N  A  Q  R  F  G  I  S  N  Y  C  Q  I  Y
ccaccaaatgcaaacaaaattcgtgaagctttggctcaaacccacagcgctattgccgtc
P  P  N  A  N  K  I  R  E  A  L  A  Q  T  H  S  A  I  A  V
attattggcatcaaagatttagacgcttttccgtcattatgatggccgaacaatcattcaa
I  I  G  I  K  D  L  D  A  F  R  H  Y  D  G  R  T  I  I  Q
cgcgataatggttaccaaccaaactatcacgctgtcaacattgttggttacagtaacgca
R  D  N  G  Y  Q  P  N  Y  H  A  V  N  I  V  G  Y  S  N  A
cagggtgtcgattattggatcgtacgaaacagttgggataccaattggggtgataatggt
Q  G  V  D  Y  W  I  V  R  N  S  W  D  T  N  W  G  D  N  G
tacggttattttgctgccaacatcgatttgatgatgattgaagaatatccatatgttgtc
Y  G  Y  F  A  A  N  I  D  L  M  M  I  E  E  Y  P  Y  V  V
attctctaa
I  L  -
```

FIG. 1

```
gatcaagtcgatgtcaaagattgtgccaatcatgaaatcaaaaaagttttggtaccagga
 D  Q  V  D  V  K  D  C  A  N  H  E  I  K  K  V  L  V  P  G
tgccatggttcagaaccatgtatcattcatcgtggtaaaccattccaattggaagccgtt
 C  H  G  S  E  P  C  I  I  H  R  G  K  P  F  Q  L  E  A  V
ttcgaagccaaccaaaactcaaaaaccgctaaaattgaaatcaaagcttcaatcgatggt
 F  E  A  N  Q  N  S  K  T  A  K  I  E  I  K  A  S  I  D  G
ttagaagttgatgttcccggtatcgatccaaatgcatgccattatatgaaatgtccattg
 L  E  V  D  V  P  G  I  D  P  N  A  C  H  Y  M  K  C  P  L
gttaaaggacaacaatatgatattaaatatacatggaatgttccgaaaattgcaccaaaa
 V  K  G  Q  Q  Y  D  I  K  Y  T  W  N  V  P  K  I  A  P  K
tctgaaaatgttgtcgtcactgttaaagttatgggtgataatggtgttttggcctgtgct
 S  E  N  V  V  V  T  V  K  V  M  G  D  N  G  V  L  A  C  A
attgctactcatgctaaaatccgcgattaa
 I  A  T  H  A  K  I  R  D  -
```

FIG. 2

```
gtcaaagatagtgccaatcatgaaatcaaaaaagttttggtaccaggatgccatggttca
 V  K  D  S  A  N  H  E  I  K  K  V  L  V  P  G  C  H  G  S
gaaccatgtatcattcatcgtggtaaaccattccaattggaagccgttttcgaagccaac
 E  P  C  I  I  H  R  G  K  P  F  Q  L  E  A  V  F  E  A  N
caaaaactcaaaaaccgctaaaattgaaatcaaagcttcaatcgatggtttagaagttgat
 Q  N  S  K  T  A  K  I  E  I  K  A  S  I  D  G  L  E  V  D
gttcccggtatcgatccaaatgcatgccattatatgaaatgtccattggttaaaggacaa
 V  P  G  I  D  P  N  A  C  H  Y  M  K  C  P  L  V  K  G  Q
caatatgatattaaatatacatggaatgttccgaaaattgcaccaaaatctgaaaatgtt
 Q  Y  D  I  K  Y  T  W  N  V  P  K  I  A  P  K  S  E  N  V
gtcgtcactgttaaagttatgggtgataatggtgttttggccagtgctattgctacctgc
 V  V  T  V  K  V  M  G  D  N  G  V  L  A  S  A  I  A  T  C
agtatcaatggaaatgctccagctgaaatcgatttgcgacaaatgcgaactgtcactccc
 S  I  N  G  N  A  P  A  E  I  D  L  R  Q  M  R  T  V  T  P
attcgtatgcaaggaggctgtggttcatgttgggctttctctggtgttgccgcaactgaa
 I  R  M  Q  G  G  C  G  S  C  W  A  F  S  G  V  A  A  T  E
tcagcttatttggcttaccgtaatcaatcattggatcttgctgaacaagaattagtcgat
 S  A  Y  L  A  Y  R  N  Q  S  L  D  L  A  E  Q  E  L  V  D
tgtgcttcccaacacggttgtaatggtgataccattccacgtggtattgaatacatccaa
 C  A  S  Q  H  G  C  N  G  D  T  I  P  R  G  I  E  Y  I  Q
cataatggtgtcgtccaagaaagctactatcgatacgttgcacgagaacaatcatgccga
 H  N  G  V  V  Q  E  S  Y  Y  R  Y  V  A  R  E  Q  S  C  R
cgaccaaatgcacaacgtttcggtatctcaaactattgccaaatttacccaccaaatgca
 R  P  N  A  Q  R  F  G  I  S  N  Y  C  Q  I  Y  P  P  N  A
aacaaaattcgtgaagctttggctcaaacccacagcgctattgccgtcattattggcatc
 N  K  I  R  E  A  L  A  Q  T  H  S  A  I  A  V  I  I  G  I
aaagatttagacgcttttccgtcattatgatggccgaacaatcattcaacgcgataatggt
 K  D  L  D  A  F  R  H  Y  D  G  R  T  I  I  Q  R  D  N  G
taccaaccaaactatcacgctgtcaacattgttggttacagtaacgcacagggtgtcgat
 Y  Q  P  N  Y  H  A  V  N  I  V  G  Y  S  N  A  Q  G  V  D
tattggatcgtacgaaacagttgggataccaattggggtgataatggttacggttatttt
 Y  W  I  V  R  N  S  W  D  T  N  W  G  D  N  G  Y  G  Y  F
gctgccaacatcgatttgatgatgattgaagaatatccatatgttgtcattctctaa
 A  A  N  I  D  L  M  M  I  E  E  Y  P  Y  V  V  I  L  -
```

FIG. 4

```
gatcaagtcgatgtcaaagattgtgccaatcatgaaatcaaaaaagttttggtaccagga
 D  Q  V  D  V  K  D  C  A  N  H  E  I  K  K  V  L  V  P  G
tgccatggttcagaaccatgtatcattcatcgtggtaaaccattccaattggaagccgtt
 C  H  G  S  E  P  C  I  I  H  R  G  K  P  F  Q  L  E  A  V
ttcgaagccaaccaaaactcaaaaaccgctaaaattgaaatcaaagcttcaatcgatggt
 F  E  A  N  Q  N  S  K  T  A  K  I  E  I  K  A  S  I  D  G
ttagaagttgatgttcccggtatcgatccaaatggctgcagtatcaatggaaatgctcca
 L  E  V  D  V  P  G  I  D  P  N  G  C  S  I  N  G  N  A  P
gctgaaatcgatttgcgacaaatgcgaactgtcactcccattcgtatgcaaggaggctgt
 A  E  I  D  L  R  Q  M  R  T  V  T  P  I  R  M  Q  G  G  C
ggttcatgttgggctttctctggtgttgccgcaactgaatcagcttatttggcttaccgt
 G  S  C  W  A  F  S  G  V  A  A  T  E  S  A  Y  L  A  Y  R
aatcaatcattggatcttgctgaacaagaattagtcgattgtgcttcccaacacggttgt
 N  Q  S  L  D  L  A  E  Q  E  L  V  D  C  A  S  Q  H  G  C
aatggtgataccattccacgtggtattgaatacatccaacataatggtgtcgtccaagaa
 N  G  D  T  I  P  R  G  I  E  Y  I  Q  H  N  G  V  V  Q  E
agctactatcgatacgttgcacgagaacaatcatgccgacgaccaaatgcacaacgtttc
 S  Y  Y  R  Y  V  A  R  E  Q  S  C  R  R  P  N  A  Q  R  F
ggtatctcaaactattgccaaatttacccaccaaatgcaaacaaaattcgtgaagctttg
 G  I  S  N  Y  C  Q  I  Y  P  P  N  A  N  K  I  R  E  A  L
gctcaaacccacagcgctattgccgtcattattggcatcaaagatttagacgctttccgt
 A  Q  T  H  S  A  I  A  V  I  I  G  I  K  D  L  D  A  F  R
cattatgatggccgaacaatcattcaacgcgataatggttaccaaccaaactatcacgct
 H  Y  D  G  R  T  I  I  Q  R  D  N  G  Y  Q  P  N  Y  H  A
gtcaacattgttggttacagtaacgcacagggtgtcgattattggatcgtacgaaacagt
 V  N  I  V  G  Y  S  N  A  Q  G  V  D  Y  W  I  V  R  N  S
tgggataccaattggggtgataatggttacggttattttgctgccaacatcgatttgatg
 W  D  T  N  W  G  D  N  G  Y  G  Y  F  A  A  N  I  D  L  M
atgattgaagaatatccatatgttgtcattctccctaggcattacatgaaaagcccattg
 M  I  E  E  Y  P  Y  V  V  I  L  P  R  H  Y  M  K  S  P  L
gttaaaggacaacaatatgatattaaatatacatggaatgttccgaaaattgcaccaaaa
 V  K  G  Q  Q  Y  D  I  K  Y  T  W  N  V  P  K  I  A  P  K
tctgaaaatgttgtcgtcactgttaaagttatgggtgataatggtgttttggcctgtgct
 S  E  N  V  V  V  T  V  K  V  M  G  D  N  G  V  L  A  C  A
attgttactcatgctaaaatccgcgattaa
 I  V  T  H  A  K  I  R  D  -
```

FIG. 6

SEQUENCE LISTING

```
<160> NUMBER OF SEQ ID NOS: 17

<210> SEQ ID NO 1
<211> LENGTH: 1017
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1014)

<400> SEQUENCE: 1 gtc aaa gat agt gcc aat cat gaa atc aaa aaa gtt ttg gta cca gga        48
Val Lys Asp Ser Ala Asn His Glu Ile Lys Lys Val Leu Val Pro Gly
1               5                   10                  15 tgc cat ggt tca gaa cca tgt atc att cat cgt ggt aaa cca ttc caa        96
Cys His Gly Ser Glu Pro Cys Ile Ile His Arg Gly Lys Pro Phe Gln
                20                  25                  30 ttg gaa gcc gtt ttc gaa gcc aac caa aac tca aaa acc gct aaa att       144
Leu Glu Ala Val Phe Glu Ala Asn Gln Asn Ser Lys Thr Ala Lys Ile
            35                  40                  45 gaa atc aaa gct tca atc gat ggt tta gaa gtt gat gtt ccc ggt atc       192
Glu Ile Lys Ala Ser Ile Asp Gly Leu Glu Val Asp Val Pro Gly Ile
        50                  55                  60 gat cca aat gca tgc cat tat atg aaa tgt cca ttg gtt aaa gga caa       240
Asp Pro Asn Ala Cys His Tyr Met Lys Cys Pro Leu Val Lys Gly Gln
65                  70                  75                  80 caa tat gat att aaa tat aca tgg aat gtt ccg aaa att gca cca aaa       288
Gln Tyr Asp Ile Lys Tyr Thr Trp Asn Val Pro Lys Ile Ala Pro Lys
                85                  90                  95 tct gaa aat gtt gtc gtc act gtt aaa gtt atg ggt gat aat ggt gtt       336
Ser Glu Asn Val Val Val Thr Val Lys Val Met Gly Asp Asn Gly Val
                100                 105                 110 ttg gcc agt gct att gct acc tgc agt atc aat gga aat gct cca gct       384
Leu Ala Ser Ala Ile Ala Thr Cys Ser Ile Asn Gly Asn Ala Pro Ala
            115                 120                 125
```

```
gaa atc gat ttg cga caa atg cga act gtc act ccc att cgt atg caa    432
Glu Ile Asp Leu Arg Gln Met Arg Thr Val Thr Pro Ile Arg Met Gln
130                 135                 140 gga ggc tgt ggt tca tgt tgg gct ttc tct ggt gtt gcc gca act gaa    480
Gly Gly Cys Gly Ser Cys Trp Ala Phe Ser Gly Val Ala Ala Thr Glu
145                 150                 155                 160 tca gct tat ttg gct tac cgt aat caa tca ttg gat ctt gct gaa caa    528
Ser Ala Tyr Leu Ala Tyr Arg Asn Gln Ser Leu Asp Leu Ala Glu Gln
                165                 170                 175 gaa tta gtc gat tgt gct tcc caa cac ggt tgt aat ggt gat acc att    576
Glu Leu Val Asp Cys Ala Ser Gln His Gly Cys Asn Gly Asp Thr Ile
            180                 185                 190 cca cgt ggt att gaa tac atc caa cat aat ggt gtc gtc caa gaa agc    624
Pro Arg Gly Ile Glu Tyr Ile Gln His Asn Gly Val Val Gln Glu Ser
        195                 200                 205 tac tat cga tac gtt gca cga gaa caa tca tgc cga cga cca aat gca    672
Tyr Tyr Arg Tyr Val Ala Arg Glu Gln Ser Cys Arg Arg Pro Asn Ala
210                 215                 220 caa cgt ttc ggt atc tca aac tat tgc caa att tac cca cca aat gca    720
Gln Arg Phe Gly Ile Ser Asn Tyr Cys Gln Ile Tyr Pro Pro Asn Ala
225                 230                 235                 240 aac aaa att cgt gaa gct ttg gct caa acc cac agc gct att gcc gtc    768
Asn Lys Ile Arg Glu Ala Leu Ala Gln Thr His Ser Ala Ile Ala Val
                245                 250                 255 att att ggc atc aaa gat tta gac gct ttc cgt cat tat gat ggc cga    816
Ile Ile Gly Ile Lys Asp Leu Asp Ala Phe Arg His Tyr Asp Gly Arg
            260                 265                 270 aca atc att caa cgc gat aat ggt tac caa cca aac tat cac gct gtc    864
Thr Ile Ile Gln Arg Asp Asn Gly Tyr Gln Pro Asn Tyr His Ala Val
        275                 280                 285 aac att gtt ggt tac agt aac gca cag ggt gtc gat tat tgg atc gta    912
Asn Ile Val Gly Tyr Ser Asn Ala Gln Gly Val Asp Tyr Trp Ile Val
290                 295                 300 cga aac agt tgg gat acc aat tgg ggt gat aat ggt tac ggt tat ttt    960
Arg Asn Ser Trp Asp Thr Asn Trp Gly Asp Asn Gly Tyr Gly Tyr Phe
305                 310                 315                 320 gct gcc aac atc gat ttg atg atg att gaa gaa tat cca tat gtt gtc   1008
Ala Ala Asn Ile Asp Leu Met Met Ile Glu Glu Tyr Pro Tyr Val Val
                325                 330                 335 att ctc taa                                                        1017
Ile Leu

<210> SEQ ID NO 2
<211> LENGTH: 338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Val Lys Asp Ser Ala Asn His Glu Ile Lys Lys Val Leu Val Pro Gly
1               5                   10                  15

Cys His Gly Ser Glu Pro Cys Ile Ile His Arg Gly Lys Pro Phe Gln
                20                  25                  30

Leu Glu Ala Val Phe Glu Ala Asn Gln Asn Ser Lys Thr Ala Lys Ile
            35                  40                  45

Glu Ile Lys Ala Ser Ile Asp Gly Leu Glu Val Asp Val Pro Gly Ile
        50                  55                  60
```

```
Asp Pro Asn Ala Cys His Tyr Met Lys Cys Pro Leu Val Lys Gly Gln
 65                  70                  75                  80

Gln Tyr Asp Ile Lys Tyr Thr Trp Asn Val Pro Lys Ile Ala Pro Lys
                 85                  90                  95

Ser Glu Asn Val Val Thr Val Lys Val Met Gly Asp Asn Gly Val
            100                 105                 110

Leu Ala Ser Ala Ile Ala Thr Cys Ser Ile Asn Gly Asn Ala Pro Ala
            115                 120                 125

Glu Ile Asp Leu Arg Gln Met Arg Thr Val Thr Pro Ile Arg Met Gln
        130                 135                 140

Gly Gly Cys Gly Ser Cys Trp Ala Phe Ser Gly Val Ala Ala Thr Glu
145                 150                 155                 160

Ser Ala Tyr Leu Ala Tyr Arg Asn Gln Ser Leu Asp Leu Ala Glu Gln
                165                 170                 175

Glu Leu Val Asp Cys Ala Ser Gln His Gly Cys Asn Gly Asp Thr Ile
            180                 185                 190

Pro Arg Gly Ile Glu Tyr Ile Gln His Asn Gly Val Val Gln Glu Ser
        195                 200                 205

Tyr Tyr Arg Tyr Val Ala Arg Glu Gln Ser Cys Arg Arg Pro Asn Ala
210                 215                 220

Gln Arg Phe Gly Ile Ser Asn Tyr Cys Gln Ile Tyr Pro Pro Asn Ala
225                 230                 235                 240

Asn Lys Ile Arg Glu Ala Leu Ala Gln Thr His Ser Ala Ile Ala Val
                245                 250                 255

Ile Ile Gly Ile Lys Asp Leu Asp Ala Phe Arg His Tyr Asp Gly Arg
            260                 265                 270

Thr Ile Ile Gln Arg Asp Asn Gly Tyr Gln Pro Asn Tyr His Ala Val
        275                 280                 285

Asn Ile Val Gly Tyr Ser Asn Ala Gln Gly Val Asp Tyr Trp Ile Val
        290                 295                 300

Arg Asn Ser Trp Asp Thr Asn Trp Gly Asp Asn Gly Tyr Gly Tyr Phe
305                 310                 315                 320

Ala Ala Asn Ile Asp Leu Met Met Ile Glu Glu Tyr Pro Tyr Val Val
                325                 330                 335

Ile Leu

<210> SEQ ID NO 3
<211> LENGTH: 1050
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1047)

<400> SEQUENCE: 3 gat caa gtc gat gtc aaa gat tgt gcc aat cat gaa atc aaa aaa gtt      48
Asp Gln Val Asp Val Lys Asp Cys Ala Asn His Glu Ile Lys Lys Val
  1               5                  10                  15 ttg gta cca gga tgc cat ggt tca gaa cca tgt atc att cat cgt ggt      96
Leu Val Pro Gly Cys His Gly Ser Glu Pro Cys Ile Ile His Arg Gly
             20                  25                  30 aaa cca ttc caa ttg gaa gcc gtt ttc gaa gcc aac caa aac tca aaa     144
Lys Pro Phe Gln Leu Glu Ala Val Phe Glu Ala Asn Gln Asn Ser Lys
         35                  40                  45
```

| | |
|---|---|
| acc gct aaa att gaa atc aaa gct tca atc gat ggt tta gaa gtt gat<br>Thr Ala Lys Ile Glu Ile Lys Ala Ser Ile Asp Gly Leu Glu Val Asp<br>50 55 60 | 192 |
| gtt ccc ggt atc gat cca aat ggc tgc agt atc aat gga aat gct cca<br>Val Pro Gly Ile Asp Pro Asn Gly Cys Ser Ile Asn Gly Asn Ala Pro<br>65 70 75 80 | 240 |
| gct gaa atc gat ttg cga caa atg cga act gtc act ccc att cgt atg<br>Ala Glu Ile Asp Leu Arg Gln Met Arg Thr Val Thr Pro Ile Arg Met<br>85 90 95 | 288 |
| caa gga ggc tgt ggt tca tgt tgg gct ttc tct ggt gtt gcc gca act<br>Gln Gly Gly Cys Gly Ser Cys Trp Ala Phe Ser Gly Val Ala Ala Thr<br>100 105 110 | 336 |
| gaa tca gct tat ttg gct tac cgt aat caa tca ttg gat ctt gct gaa<br>Glu Ser Ala Tyr Leu Ala Tyr Arg Asn Gln Ser Leu Asp Leu Ala Glu<br>115 120 125 | 384 |
| caa gaa tta gtc gat tgt gct tcc caa cac ggt tgt aat ggt gat acc<br>Gln Glu Leu Val Asp Cys Ala Ser Gln His Gly Cys Asn Gly Asp Thr<br>130 135 140 | 432 |
| att cca cgt ggt att gaa tac atc caa cat aat ggt gtc gtc caa gaa<br>Ile Pro Arg Gly Ile Glu Tyr Ile Gln His Asn Gly Val Val Gln Glu<br>145 150 155 160 | 480 |
| agc tac tat cga tac gtt gca cga gaa caa tca tgc cga cga cca aat<br>Ser Tyr Tyr Arg Tyr Val Ala Arg Glu Gln Ser Cys Arg Arg Pro Asn<br>165 170 175 | 528 |
| gca caa cgt ttc ggt atc tca aac tat tgc caa att tac cca cca aat<br>Ala Gln Arg Phe Gly Ile Ser Asn Tyr Cys Gln Ile Tyr Pro Pro Asn<br>180 185 190 | 576 |
| gca aac aaa att cgt gaa gct ttg gct caa acc cac agc gct att gcc<br>Ala Asn Lys Ile Arg Glu Ala Leu Ala Gln Thr His Ser Ala Ile Ala<br>195 200 205 | 624 |
| gtc att att ggc atc aaa gat tta gac gct ttc cgt cat tat gat ggc<br>Val Ile Ile Gly Ile Lys Asp Leu Asp Ala Phe Arg His Tyr Asp Gly<br>210 215 220 | 672 |
| cga aca atc att caa cgc gat aat ggt tac caa cca aac tat cac gct<br>Arg Thr Ile Ile Gln Arg Asp Asn Gly Tyr Gln Pro Asn Tyr His Ala<br>225 230 235 240 | 720 |
| gtc aac att gtt ggt tac agt aac gca cag ggt gtc gat tat tgg atc<br>Val Asn Ile Val Gly Tyr Ser Asn Ala Gln Gly Val Asp Tyr Trp Ile<br>245 250 255 | 768 |
| gta cga aac agt tgg gat acc aat tgg ggt gat aat ggt tac ggt tat<br>Val Arg Asn Ser Trp Asp Thr Asn Trp Gly Asp Asn Gly Tyr Gly Tyr<br>260 265 270 | 816 |
| ttt gct gcc aac atc gat ttg atg atg att gaa gaa tat cca tat gtt<br>Phe Ala Ala Asn Ile Asp Leu Met Met Ile Glu Glu Tyr Pro Tyr Val<br>275 280 285 | 864 |
| gtc att ctc cct agg cat tac atg aaa agc cca ttg gtt aaa gga caa<br>Val Ile Leu Pro Arg His Tyr Met Lys Ser Pro Leu Val Lys Gly Gln<br>290 295 300 | 912 |
| caa tat gat att aaa tat aca tgg aat gtt ccg aaa att gca cca aaa<br>Gln Tyr Asp Ile Lys Tyr Thr Trp Asn Val Pro Lys Ile Ala Pro Lys<br>305 310 315 320 | 960 |
| tct gaa aat gtt gtc gtc act gtt aaa gtt atg ggt gat aat ggt gtt<br>Ser Glu Asn Val Val Val Thr Val Lys Val Met Gly Asp Asn Gly Val<br>325 330 335 | 1008 |
| ttg gcc tgt gct att gtt act cat gct aaa atc cgc gat taa<br>Leu Ala Cys Ala Ile Val Thr His Ala Lys Ile Arg Asp<br>340 345 | 1050 |

<210> SEQ ID NO 4
<211> LENGTH: 349

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Ser Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Gly Cys Ser Ile Asn Gly Asn Ala Pro
65                  70                  75                  80

Ala Glu Ile Asp Leu Arg Gln Met Arg Thr Val Thr Pro Ile Arg Met
                85                  90                  95

Gln Gly Gly Cys Gly Ser Cys Trp Ala Phe Ser Gly Val Ala Ala Thr
            100                 105                 110

Glu Ser Ala Tyr Leu Ala Tyr Arg Asn Gln Ser Leu Asp Leu Ala Glu
        115                 120                 125

Gln Glu Leu Val Asp Cys Ala Ser Gln His Gly Cys Asn Gly Asp Thr
130                 135                 140

Ile Pro Arg Gly Ile Glu Tyr Ile Gln His Asn Gly Val Val Gln Glu
145                 150                 155                 160

Ser Tyr Tyr Arg Tyr Val Ala Arg Glu Gln Ser Cys Arg Arg Pro Asn
                165                 170                 175

Ala Gln Arg Phe Gly Ile Ser Asn Tyr Cys Gln Ile Tyr Pro Pro Asn
            180                 185                 190

Ala Asn Lys Ile Arg Glu Ala Leu Ala Gln Thr His Ser Ala Ile Ala
        195                 200                 205

Val Ile Ile Gly Ile Lys Asp Leu Asp Ala Phe Arg His Tyr Asp Gly
    210                 215                 220

Arg Thr Ile Ile Gln Arg Asp Asn Gly Tyr Gln Pro Asn Tyr His Ala
225                 230                 235                 240

Val Asn Ile Val Gly Tyr Ser Asn Ala Gln Gly Val Asp Tyr Trp Ile
                245                 250                 255

Val Arg Asn Ser Trp Asp Thr Asn Trp Gly Asp Asn Gly Tyr Gly Tyr
            260                 265                 270

Phe Ala Ala Asn Ile Asp Leu Met Met Ile Glu Glu Tyr Pro Tyr Val
        275                 280                 285

Val Ile Leu Pro Arg His Tyr Met Lys Ser Pro Leu Val Lys Gly Gln
    290                 295                 300

Gln Tyr Asp Ile Lys Tyr Thr Trp Asn Val Pro Lys Ile Ala Pro Lys
305                 310                 315                 320

Ser Glu Asn Val Val Val Thr Val Lys Val Met Gly Asp Asn Gly Val
                325                 330                 335

Leu Ala Cys Ala Ile Val Thr His Ala Lys Ile Arg Asp
            340                 345

<210> SEQ ID NO 5
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 5
actgacaggc ctcgtccatc atcgatcaaa ac                                    32

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggaattcct aggttagaga atgacaacat atgg                                  34

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgggatccga tcaagtcgat gtcaaag                                          27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggaattctt aatcgcggat tttagc                                           26

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgggatccgt caaagatagt gccaatc                                          27

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acggatctgc aggtagcaat agcactggcc aa                                    32

<210> SEQ ID NO 11
<211> LENGTH: 34
<212> TYPE: DNA
<213> ORGANISM: Artificial Sequence
<220> FEATURE:
```

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ccgaattccc taggctgcag ccatttggat cgat    34

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
cacctaggga gaatgacaac atatgg    26

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
cctaggcatt acatgaaaag ccca    24

<210> SEQ ID NO 14
<211> LENGTH: 909
<212> TYPE: DNA
<213> ORGANISM: Dermatophagoides pteronyssinus
<220> FEATURE:
<221> NAME/KEY: CDS
<222> LOCATION: (1)..(906)

<400> SEQUENCE: 14

```
cgt cca tca tcg atc aaa act ttt gaa gaa tac aaa aaa gcc ttc aac     48
Arg Pro Ser Ser Ile Lys Thr Phe Glu Glu Tyr Lys Lys Ala Phe Asn
1               5                   10                  15 aaa agt tat gct acc ttc gaa gat gaa gaa gct gcc cgt aaa aac ttt     96
Lys Ser Tyr Ala Thr Phe Glu Asp Glu Glu Ala Ala Arg Lys Asn Phe
            20                  25                  30 ttg gaa tca gta aaa tat gtt caa tca aac gga ggt gcc atc aac cat    144
Leu Glu Ser Val Lys Tyr Val Gln Ser Asn Gly Gly Ala Ile Asn His
        35                  40                  45 ttg tcc gat ttg tcg ttg gat gaa ttc aaa aac cga ttc ttg atg agt    192
Leu Ser Asp Leu Ser Leu Asp Glu Phe Lys Asn Arg Phe Leu Met Ser
    50                  55                  60 gca gaa gct ttt gaa cac ctc aaa act caa ttc gat ttg aat gct gaa    240
Ala Glu Ala Phe Glu His Leu Lys Thr Gln Phe Asp Leu Asn Ala Glu
65                  70                  75                  80 act aac gcc tgc agt atc aat gga aat gct cca gct gaa atc gat ttg    288
Thr Asn Ala Cys Ser Ile Asn Gly Asn Ala Pro Ala Glu Ile Asp Leu
                85                  90                  95 cga caa atg cga act gtc act ccc att cgt atg caa gga ggc tgt ggt    336
Arg Gln Met Arg Thr Val Thr Pro Ile Arg Met Gln Gly Gly Cys Gly
            100                 105                 110 tca tgt tgg gct ttc tct ggt gtt gcc gca act gaa tca gct tat ttg    384
Ser Cys Trp Ala Phe Ser Gly Val Ala Ala Thr Glu Ser Ala Tyr Leu
        115                 120                 125 gct tac cgt aat caa tca ttg gat ctt gct gaa caa gaa tta gtc gat    432
Ala Tyr Arg Asn Gln Ser Leu Asp Leu Ala Glu Gln Glu Leu Val Asp
    130                 135                 140
```

```
tgt gct tcc caa cac ggt tgt aat ggt gat acc att cca cgt ggt att      480
Cys Ala Ser Gln His Gly Cys Asn Gly Asp Thr Ile Pro Arg Gly Ile
145                 150                 155                 160 gaa tac atc caa cat aat ggt gtc gtc caa gaa agc tac tat cga tac      528
Glu Tyr Ile Gln His Asn Gly Val Val Gln Glu Ser Tyr Tyr Arg Tyr
                165                 170                 175 gtt gca cga gaa caa tca tgc cga cga cca aat gca caa cgt ttc ggt      576
Val Ala Arg Glu Gln Ser Cys Arg Arg Pro Asn Ala Gln Arg Phe Gly
            180                 185                 190 atc tca aac tat tgc caa att tac cca cca aat gca aac aaa att cgt      624
Ile Ser Asn Tyr Cys Gln Ile Tyr Pro Pro Asn Ala Asn Lys Ile Arg
        195                 200                 205 gaa gct ttg gct caa acc cac agc gct att gcc gtc att att ggc atc      672
Glu Ala Leu Ala Gln Thr His Ser Ala Ile Ala Val Ile Ile Gly Ile
    210                 215                 220 aaa gat tta gac gct ttc cgt cat tat gat ggc cga aca atc att caa      720
Lys Asp Leu Asp Ala Phe Arg His Tyr Asp Gly Arg Thr Ile Ile Gln
225                 230                 235                 240 cgc gat aat ggt tac caa cca aac tat cac gct gtc aac att gtt ggt      768
Arg Asp Asn Gly Tyr Gln Pro Asn Tyr His Ala Val Asn Ile Val Gly
                245                 250                 255 tac agt aac gca cag ggt gtc gat tat tgg atc gta cga aac agt tgg      816
Tyr Ser Asn Ala Gln Gly Val Asp Tyr Trp Ile Val Arg Asn Ser Trp
            260                 265                 270 gat acc aat tgg ggt gat aat ggt tac ggt tat ttt gct gcc aac atc      864
Asp Thr Asn Trp Gly Asp Asn Gly Tyr Gly Tyr Phe Ala Ala Asn Ile
        275                 280                 285 gat ttg atg atg att gaa gaa tat cca tat gtt gtc att ctc taa          909
Asp Leu Met Met Ile Glu Glu Tyr Pro Tyr Val Val Ile Leu
    290                 295                 300

<210> SEQ ID NO 15
<211> LENGTH: 302
<212> TYPE: PRT
<213> ORGANISM: Dermatophagoides pteronyssinus

<400> SEQUENCE: 15

Arg Pro Ser Ser Ile Lys Thr Phe Glu Glu Tyr Lys Lys Ala Phe Asn
1               5                   10                  15

Lys Ser Tyr Ala Thr Phe Glu Asp Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Cys Ser Ile Asn Gly Asn Ala Pro Ala Glu Ile Asp Leu
                85                  90                  95

Arg Gln Met Arg Thr Val Thr Pro Ile Arg Met Gln Gly Gly Cys Gly
            100                 105                 110

Ser Cys Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
    130                 135                 140

Cys Ala Ser Gln His Gly Cys Asn Gly Asp Thr Ile Pro Arg Gly Ile
145                 150                 155                 160
```

```
Glu Tyr Ile Gln His Asn Gly Val Val Gln Glu Ser Tyr Tyr Arg Tyr
                165                 170                 175

Val Ala Arg Glu Gln Ser Cys Arg Arg Pro Asn Ala Gln Arg Phe Gly
            180                 185                 190

Ile Ser Asn Tyr Cys Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300

<210> SEQ ID NO 16
<211> LENGTH: 390
<212> TYPE: DNA
<213> ORGANISM: Dermatophagoides pteronyssinus
<220> FEATURE:
<221> NAME/KEY: CDS
<222> LOCATION: (1)..(387)

<400> SEQUENCE: 16 gat caa gtc gat gtc aaa gat tgt gcc aat cat gaa atc aaa aaa gtt      48
Asp Gln Val Asp Val Lys Asp Cys Ala Asn His Glu Ile Lys Lys Val
1               5                   10                  15 ttg gta cca gga tgc cat ggt tca gaa cca tgt atc att cat cgt ggt      96
Leu Val Pro Gly Cys His Gly Ser Glu Pro Cys Ile Ile His Arg Gly
                20                  25                  30 aaa cca ttc caa ttg gaa gcc gtt ttc gaa gcc aac caa aac tca aaa     144
Lys Pro Phe Gln Leu Glu Ala Val Phe Glu Ala Asn Gln Asn Ser Lys
            35                  40                  45 acc gct aaa att gaa atc aaa gct tca atc gat ggt tta gaa gtt gat     192
Thr Ala Lys Ile Glu Ile Lys Ala Ser Ile Asp Gly Leu Glu Val Asp
        50                  55                  60 gtt ccc ggt atc gat cca aat gca tgc cat tat atg aaa tgt cca ttg     240
Val Pro Gly Ile Asp Pro Asn Ala Cys His Tyr Met Lys Cys Pro Leu
65                  70                  75                  80 gtt aaa gga caa caa tat gat att aaa tat aca tgg aat gtt ccg aaa     288
Val Lys Gly Gln Gln Tyr Asp Ile Lys Tyr Thr Trp Asn Val Pro Lys
                85                  90                  95 att gca cca aaa tct gaa aat gtt gtc gtc act gtt aaa gtt atg ggt     336
Ile Ala Pro Lys Ser Glu Asn Val Val Val Thr Val Lys Val Met Gly
            100                 105                 110 gat aat ggt gtt ttg gcc tgt gct att gct act cat gct aaa atc cgc     384
Asp Asn Gly Val Leu Ala Cys Ala Ile Ala Thr His Ala Lys Ile Arg
        115                 120                 125 gat taa                                                             390
Asp

<210> SEQ ID NO 17
<211> LENGTH: 129
<212> TYPE: PRT
<213> ORGANISM: Dermatophagoides pteronyssinus
```

```
<400> SEQUENCE: 17

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Ser Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asn Gly Val Leu Ala Cys Ala Ile Ala Thr His Ala Lys Ile Arg
        115                 120                 125

Asp
```

HYPOALLERGENIC HYBRID PROTEINS OF MAJOR GROUP 1 AND 2 MITE ALLERGENS FOR USE IN THE TREATMENT OF ALLERGIES

FIELD OF THE INVENTION

The present invention relates to the field of hybrid protein production for the prevention and treatment of allergies, particularly allergies caused by house dust mites, and more particularly to those caused by mites of the genus *Dermatophagoides* and more specifically to those due to sensitisation to group 1 and 2 allergens.

STATE OF THE ART

Allergy is the specific hereditary or acquired disturbance in the ability to react to foreign substances that are normally harmless (allergens). Allergy is related to inflammatory reactions of the affected organs (skin, conjunctiva, nose, pharynx, bronchial mucous membrane, gastrointestinal tract). Immediate symptoms of the disease include rhinitis, conjunctivitis, dermatitis, asthma and anaphylactic shock: and chronic manifestations of the disease include delayed reactions of asthma and atopic dermatitis. Type I allergies are a significant health problem in industrialised countries. This type of allergy is caused by the formation of IgE antibodies against airborne antigens. These IgE antibodies interact with mastocytes and basophils, releasing biological mediators such as histamine, which produce allergic rhinitis, conjunctivitis and bronchial asthma in over 25% of the population of industrialised countries. [Floistrup, H., Swartz, J., Bergstrom, A., Alm, J. S., Scheynius, A., van Hage, M., Waser, M., Braun-Fahrlander, C., Schram-Bijkerk, D., Huber, M., Zutavern, A., von Mutius, E., Ublagger, E., Riedler, J., Michaels, K. B., Pershagen, G., The Parsifal Study Group. (2006). Allergic disease and sensitization in Steiner school children. J Allergy Clin Immunol. 117, 59-66].

At present, the only treatment for allergy that is directed to the cause of the disease is allergen-specific immunotherapy (SIT). SIT is an effective treatment for allergic diseases caused by specific allergens and basically involves modulating the patient's immune response by the regular administration in increasing concentrations of the proteins that produce the allergy (allergenic extracts). Although various studies have demonstrated the clinical effectiveness of this allergen-specific immunotherapy, the immunological mechanisms thereof are not fully understood.

What is known so far is that high doses of injected allergens induce elevated synthesis of IL-12 by antigen-presenting cells, for example dendritic cells, which preferentially promote the development of naive helper T cells ($nT_H$) into $T_H1$ or $T_H0$ cells. This allows the allergic immune response related to $T_H2$ cells to be switched to a $T_H1/T_H0$ response which induces the production of high levels of IFN-γ [Akdis, C. A. and Blaser, K. (2000). Mechanisms of allergen-specific immunotherapy. Allergy 55, 522-530]. This immune switching is reinforced by the induction of tolerance (clonal anergy or clonal deletion) of $T_H2$ memory cells under the influence of regulating T cells ($T_R1$) which produce the immunosuppressive cytokines IL-10 and TGF-β [Akdis, C. A., Joss, A., Akdis, M., and Blaser, K. (2001). Mechanism of IL-10 induced cell inactivation in allergic inflammation and normal response to allergens. Int. Arch Allergy Immunol. 124; 180-182]. The decline in the activation and proliferation of $T_H2$ cells results in lower production of IL-4, and of IgEs by the B cells. The decline in the activation and infiltration of $T_H2$ cells in the nasal and bronchial mucous membrane results in lower synthesis of IL-5, allowing a reduction in the infiltration of eosinophils which leads to a large reduction in the release of inflammatory mediators such as the MBP (major basic protein) and ECP (eosinophil cationic protein). The new allergen-specific clones of T cells of predominant phenotype $T_H0$ produce a mixture of $T_H1$ and $T_H2$ cytokines promoting the production by the B cells of a large quantity of allergen-specific IgG antibodies. In addition, the high levels of IL-10 induce elevated synthesis of allergen-specific IgG4 antibodies. These two types of specific antibodies can act as blocking antibodies preventing the crosslinking of IgE-bound receptors anchored on the mastocytes, and thus inhibiting the degranulation and release of histamine [Moverare, R. (2003). Immunological mechanisms of specific immunotherapy with pollen vaccines: implications for diagnostics and the development of improved vaccination strategies. Expert Rev. Vacc. 2, 85-97; Wachholz, P. A., Soni, N. K., Till, S., and Durham, S. R. (2003). Inhibition of allergen-IgE binding to B cells by IgG antibodies after grass pollen immunotherapy. J. Allergy Clin. Immunol. 112; 915-922]. They also block IgE-mediated antigen capture by the antigen-presenting cells, and this suppresses the immune reaction to the allergens.

Allergenic extracts isolated from natural sources are complex mixtures of proteins and other molecules. The composition, and hence the allergenicity thereof, depends on the material used, which varies according to environmental conditions in the case of pollens, the maturation phase in the case of fungi, the growth conditions of mites, etc. In addition, some extracts may contain an insufficient concentration of major allergens, they may be contaminated with undesirable components, to which the patient is not allergic, or both problems may be present. Present immunotherapy uses exclusively complete allergenic extracts, and this has a number of drawbacks such as:

Serious adverse reactions due to the reactivity of the vaccine with the IgE antibodies anchored in the effector cells.

The appearance, after immunotherapy treatment has begun, of new sensitisations to other allergens present in the vaccine.

Difficulties in the standardised production of some allergenic extracts.

All of this leads to immunotherapy not being as safe and effective a treatment as would be wished.

A better understanding of the pathogenesis of the allergy and the mechanisms of specific immunotherapy has allowed a solution to the above-mentioned problems to be approached. An understanding of the influence of the presentation of the IgE-mediated antigen in the allergen-specific $T_H2$ response has increased efforts to produce allergens that do not bind IgE. Such allergen will be directed to the T cells by an antigen-capture mechanism based on phagocytosis/pinocytosis, avoiding IgE-crosslinking and the presentation of the IgE-dependent antigen. This induces a balance in production of $T_H0$ or $T_H1$ cytokines by the T cells, and lower IgE and greater IgG production by the B cells; which would all lead to the induction of tolerance of $T_H2$-type T cells without risk of anaphylaxis.

The progress of recombinant techniques to obtain allergens and allergen derivatives has facilitated a large increase in the capacity to develop new vaccines for the treatment of allergy. The difficulty facing those working in this field is to reduce the IgE binding of the antigen, whilst retaining its recognition by T cells. Allergen molecules which have a lower IgE binding capacity but maintain their reactivity to T cells, could be administered in higher doses allowing faster and safer immunotherapy with fewer injections. In addition, the recombinant allergens can be produced on a large scale in fermentation tanks, using microbial expression systems, and the purification thereof is more efficient than that of their natural equivalents.

Mites belong to the arthropod group and have a size of less than 0.3 mm; they can be found in different environments, including house dust. They have been recognised as being responsible for house dust allergies since the late 1960s.

The principal mites responsible for producing allergic symptoms are included in the order Astigmata and their taxonomic distribution is as follows:

Kingdom Animalia
    Phylum Arthopoda
        Class Arachnida
            Subclass Acari
            Order ASTIGMATA
            Family Glycyphagidae
                Subfamily Glycyphaginae
                      Genus *Blomia*
                      *B. freemani*
                      *B. kulagini*
                      *B. tropicalis*
                      Genus *Glycyphagus*
                      *G. domesticus*
                      Genus *Lepidoglyphus*
                      *L. destructor*
                Subfamily Labidophorinae
                      Genus *Gohieria*
                      *G. fusca*
            Family Pyroglyphidae
                Subfamily Dermatophagoidinae
                      Genus *Dermatophagoides*
                      *D. evansi*
                      *D. farinae*
                      *D. microceras*
                      *D. pteronyssinus*
                      *D. siboney*
                      *D. neotropicalis*
                      Genus *Hirstia*
                      *H. domicola*
                      Genus *Malayoglyphus*
                      *M. carmelitus*
                Subfamily Pyroglyphinae
                      Genus *Euroglyphus*
                      *E. maynei*
            Family Acaridae
                Genus *Acarus*
                      *A. siro*
                Genus *Tyrophagus*
                      *T. longior*
                      *T. putrescentiae*
            Family Chortoglyphidae
                Genus *Chortoglyphus*
                    *C. arcuatus*

The species that most often produce allergy are those of the genus *Dermatophagoides*. Their optimal growth conditions are a temperature of about 20° C. and relative humidity above 70%. An environment with humidity of less than 50-60% limits their presence to an extraordinary extent; they are therefore very plentiful in temperate coastal regions, and rarely present in dry mountainous zones, particularly above an altitude of 1500 m. Thus, mite concentration also increases in houses at times of seasonal change (spring and autumn), with rain and mild temperatures, and usually decreases during the summer (hot, dry climate) and winter (cold, dry climate).

House dust mites are complex organisms which produce thousands of different proteins and other macromolecules. They are one of the most prevalent sources of allergy and it has been estimated that of the 50 million people in the EU who suffer from allergies, 15% are sensitised to mites, with approximately 10-15 million people estimated not to have been diagnosed correctly. Other data indicate that up to 80% of asthmatic children could be sensitised to mites [de Blay F, et al. Influence of mite exposure on symptoms of mite-sensitive patients with asthma. J Allergy Clin Immunol 1994; 93:136-138].

To date, 14 allergens from the most common house mites, *D. pteronyssinus* and *D. farinae*, have been described each having a very different degree of prevalence among allergic patients. The allergens of *D. pteronyssinus* described on 3 Jul. 2007 in the official list of allergens of the Allergen Nomenclature Sub-Committee (http://www.allergen.org/Allergen.aspx) of the International Union of Immunological Societies (I.U.I.S.) are:

| Der p 1 | |
|---|---|
| Biochemical name: | Cysteine protease, 28 kDa (SDS-PAGE) with a proteolytic activity that may cause an adjuvant effect in allergic processes. |
| Allergenicity: | In serum there is a positive correlation between IgE to Der p 1 and to an extract of *D. pteronyssinus*, as measured by RIA and RAST (r = 0.82, p < 0.001, n = 30). |
| | All 11 patients studied had positive skin tests in response to Der p 1 (<$10^{-2}$ μg/ml). |
| | 92% of the 42 mite-allergic patients had specific IgEs to rDer p 1 in RAST. |

| Der p 2 | |
|---|---|
| Biochemical name: | Belongs to the family NPC2, 15 kDa (SDS-PAGE). |
| Allergenicity: | 9 out of 12 mite-allergic patients (75%) had positive skin tests in response to Der p 2 (<$10^{-3}$ μg/ml). |
| | 59 out of 65 (90.7%) mite-allergic patients had specific IgEs to Der p 2 in RAST. |
| | 32 out of 45 (71%) mite-allergic patients had specific IgEs to Der p 2 in RAST. |
| | 100% of 35 mite-allergic patients had specific IgEs to Der p 2 in RAST. |

| Der p 3 | |
|---|---|
| Biochemical name: | Trypsin, 31 kDa (SDS-PAGE). |
| Allergenicity: | 100% of 55 mite-allergic patients had specific IgEs to Der p 3 in RAST. |
| | Of 35 mite-allergic patients 97% had specific IgEs to Der p 3 in RAST. |

| Der p 4 | |
|---|---|
| Biochemical name: | α-amylase, 60 kDa (SDS-PAGE). |
| Allergenicity: | On immunoblots with purified Der p 4, 46% of 27 adult mite-allergic patients had specific IgEs to Der p 4 and 25% of 20 children allergic to mites. |
| | Of 10 mite-allergic patients studied, 3 had IgEs to Der p 4 on dot-blot. |

| Der p 5 | |
|---|---|
| Size: | Protein of 14 kDa (SDS-PAGE) with no significant homology with other proteins described. |
| Allergenicity: | 6 out of 19 (31%) mite-allergic patients had specific IgEs to Der p 5 in RIA.<br>7 out of 20 mite-allergic patients (37%) had positive reactivity to Der p 5 between $10^{-4}$ and $10^{-2}$ μg/ml in skin prick tests.<br>On immunoblots, 21 out of 38 sera of mite-allergic patients recognised Der p 5. |

| Der p 6 | |
|---|---|
| Biological name: | Chemotrypsin, 25 kDa (SDS-PAGE). |
| Allergenicity: | 41% (36 of 88) of mite-allergic patients had specific IgEs to Der p 6 in RAST.<br>44% (8 of 18) of mite-allergic patients had positive reactions in subcutaneous intradermal tests with Der p 6.<br>65% of 35 mite-allergic patients were positive to Der p 6 in RAST. |

| Der p 7 | |
|---|---|
| Size: | Group of proteins of 26, 30 and 31 kDa (SDS-PAGE) with no significant homology with other proteins described. |
| Allergenicity: | 53% (16 out of 30) of the mite-allergic patients had positive reactions in subcutaneous tests with rDer p 7 (1 μg/ml).<br>14 out of 38 (37%) of children had specific IgEs to rDer p 7.<br>19 out of 41 (46%) of mite-allergic patients had specific IgEs to rDer p 7 in RIA. |

| Der p 8 | |
|---|---|
| Biochemical name: | Glutathione S-transferase, 27 kDa (SDS-PAGE). |
| Allergenicity: | 40% of patients allergic to mites recognised rDer p 8 on immunoblot. |

| Der p 9 | |
|---|---|
| Biochemical name: | Collagenolytic serine protease 29 kDa (SDS-PAGE. |
| Allergenicity: | 92% of 35 mite-allergic patients had specific IgEs to Der p 9 in RAST. |

| Der p 10 | |
|---|---|
| Biochemical name: | Tropomyosin, 36 kDa (SDS-PAGE). |
| Allergenicity: | 5.6% of mite-allergic patients had specific IgEs to recombinant Der p 10. |

| Der p 11 | |
|---|---|
| Biochemical name: | Paramyosin, 103 kDa (SDS-PAGE). |
| Allergenicity: | The prevalence of serum IgEs to Der p 11, measured on immunodot, varied between 41.7% and 66.7% depending on patient group, although it was very low in non-atopic patients with urticaria (18.8%) or normal individuals (8%). |

| Der p 14 | |
|---|---|
| Biochemical name: | Apolipophorin, 177 kDa (SDS-PAGE). |
| Allergenicity: | Der p 14 induces significant IgE responses and stimulation of T cells. |

| Der p 20 | |
|---|---|
| Biochemical name: | Arginine kinase with no size described. |

| Der p 21 |
|---|
| No data on biochemical name or molecule size. |

Der p 1 and Der p 2 react with 80-100% of mite-allergic patients [Thomas, W. R., Smith, W-E, Hale, B., Mills, K. L., O'Brien, R. M. (2002). Characterization and immunobiology of house dust mite allergens. Int. Arch. Allergy Immunol. 129; 1-8] and are capable of inhibiting almost all the IgE reactivity to the complete extract of *D. pteronyssinus* [Van der Zee, J. S., van Swieten, P., cansen, H. M., Aalbersen, R. C. (1988). Skin tests and histamine release with P1-depleted *D. pteronyssinus* body extracts and purified P1. J. Allergy Clin. Immunol. 81; 884-895; Meyer, C. H., Bond, J. F., Chen, M. C., Kasaian, M. T. (1994). Comparison of the levels of the allergens Der p I and Der p II in standardised extract of the house dust mite *D. pteronyssinus*. Clin. Exp. Allergy 24; 1041-1048].

The group 1 allergens (Der p 1) are proteins with cysteine protease activity and belong to the same family as papain and actin-cysteine protease. The mature protein has 222 residues and 80 preprotein residues. It is produced in the digestive tract of the mite and is therefore found in faeces and appears to be involved in the digestion of food. It has 3 disulphide bridges: C4-C117, C31-C71 and C64-C103 and its three-dimensional structure is composed of two globular domains: one formed at the amino-terminal end (residues 21-90) and the other at the carboxyl-terminus (residues 131-200). They are linked by a flexible loop (at positions 101-131) [Meno, K., Thorsted, P. B., Ipsen, H., Kristensen, O., Larsen, J. N., Spangfort, M. D., Gajhede, M., Lund, K. (2005). The crystal structure of recombinant proper p 1, a major house dust mite proteolytic allergen. J. Immunol. 175, 3835-3845], where great T cell stimulating activity has been demonstrated [Kircher, M. F., Haeusler, T., Nickel, R., Lamb, J. R., Renz, H., Beyer, K. (2002). Vb 18.1 and Va 2.3+ T-cell subsets are associated with house dust mite allergy in human subjects. J. Allergy Clin. Immunol. 109, 517-523]. The Der p 1 protein tends to form dimers in neutral and alkaline pH conditions. The B-cell epitopes are distributed along the whole of the molecule, some being conformational epitopes [De Halleux, S., Stura, E., VanderElst, L., Carlier, V., Jacquemin, M., Saint-Remy, J. M. (2006). Three-dimensional structure and IgE-binding properties of mature fully active Der p 1, a clinically relevant major allergen. J. Allergy Clin. Immunol. 117, 571-576].

The group 2 allergens (Der p 2) contain three disulphide bridges (C8-C119, C21-C27 and C73-C78) and are composed of two anti-parallel β sheets. The epitopes of the T cells of Der p 2 are located throughout the protein. However the peptide 111-129 is frequently recognized by T-cells [O'Brien, R. M., Thomas, W. R., Nicholson, I., Lamb, J. R., Tait, B. D. (1995). An immunogenetic analysis of the T-cell recognition of the major house dust mite allergen Der p 2: identification of high- and low-responder HLA-DQ alleles and localization of T-cell epitopes. Immunology. 86, 176-182]. The B-cell epitopes seem to be conformational since the IgE binding is highly dependent on tertiary structure.

Allergenic mite extracts are complex mixtures of proteins and non-protein molecules. The growing use of techniques for finding the levels of specific IgE relative to the components of an extract has made it possible to demonstrate that allergic patients usually react to various components. There are few cases of allergic patients who react to a single allergen. Immunotherapy studies with complete mite extracts have demonstrated that dangerous systemic adverse effects may occur during immunotherapy with mite extracts [Akçakaya, N., Hassanzadeh, A., Camcioğlu, Y., Cokuğraş, H. (2000). Local and systemic reactions during immunotherapy with adsorbed extracts of house dust mite in children Ann. Allergy Asthma Immunol. 85; 317-321] and the induction of new IgE reactivity to shellfish [van Ree, R., Antonicelli, L., Akkerdaas, J. H., Garritani, M. S., Aalberse, R. C., Bonifazi, F. (1996). Possible induction of food allergy during mite immunotherapy. Allergy 51; 108-113]. It is thus shown that the allergenic extracts known at present have clear drawbacks in achieving optimum treatment of mite allergy.

FEATURES OF THE INVENTION

Bearing in mind the above-mentioned background, the inventors have concentrated on investigating new advantageous approaches to anti-allergy treatment, particularly the treatment of allergies produced by mites. As a result of extensive investigation, the inventors have discovered a new and effective approach to the treatment of mite allergies based on new hybrid proteins formed by binding fragments of two allergens of *D. pteronyssinus* (Der p 1 and Der p 2), and various methods and means for obtaining them. The hypoallergenic hybrid proteins may have significantly reduced allergenicity compared to that of the individual native allergens and/or to mixtures thereof. For example, the hybrid proteins may have less than 60%, preferably less than 50%, more preferably less than 40%, more preferably still less than 20%, most preferably less than 10% or even less than 2% of the IgE binding capacity of the individual native allergens and/or mixtures thereof. The hybrid proteins according to the present invention may be called hypoallergenic as they have a lower capacity for binding IgE antibodies based on: i) in vitro ELISA, ELISA-inhibition and immunoblotting tests using serum pools from patients allergic to *D. pteronyssinus*; ii) in vivo skin reactivity tests on patients allergic to *D. pteronyssinus*; iii) ex vivo activation tests of basophils isolated from the blood of patients allergic to *D. pteronyssinus* and iv) in vitro EAST tests with individualised sera from patients allergic to *D. pteronyssinus*. Furthermore, the hybrid proteins according to the present invention: i) maintain their immunogenic capacity, as demonstrated by lymphoproliferation studies with peripheral blood mononuclear cells (PBMC) from 23 patients allergic to *D. pteronyssinus* showing T-cell reactivity; ii) indeed have greater immunogenicity than the wildtype proteins after immunization of mice with the hybrid proteins; and iii) have the capacity to induce 'blocking' antibodies in mice, i.e. inducing Der p 1 and Der p 2-specific IgG, which inhibit the binding of house dust-mite allergic patients' IgE to the natural allergens.

The present invention therefore relates to hybrid proteins (or chimeras) (referred to henceforward as QM1 and QM2) composed of fragments of the allergens Der p 1 and Der p 2, in which at least one of the two β sheets of Der p 2, in which the disulphide bridge between C8 and C119 of Der p 2 has been disrupted by substitution of one or both of the cystein residues at positions 8 and 119 of the mature native protein shown in FIG. 2, for example with a serine residue, or by insertion of additional amino acid sequence, such as a fragment od Der p 1 e.g. residues 5 to 222 of the mature protein (i.e. without the pre-region shown in FIG. 1). Preferably the additional amino acid sequence is inserted between residue 73 and 74 of the Der p 2 mature native protein sequence shown in FIG. 2. The allergic reactivity has been reduced, yet surprisingly without detriment to their immunogenic capacity. In fact, the hybrid proteins have shown increased immunogenicity in some tests and additionally can stimulate the production of IgG antibodies.

The invention provides therefore peptide sequences comprising or consisting of amino acid sequences that have at least 70%, preferably at least 80%, more preferably at least 90%, still more preferably at least 95%, or most preferably 100% sequence homology to SEQ ID No 2 or 4.

Said proteins may be produced by any standard protein synthesis method, for example chemical synthesis, semi-chemical synthesis or through the use of expression systems. Accordingly, the present invention also relates to the nucleotide sequences comprising or consisting of the DNA coding for said chimeric proteins, expression systems e.g. vectors comprising said sequences accompanied by the necessary sequences for expression and control of expression, and host cells and host organisms transformed by said expression systems.

The invention provides therefore polynucleotides comprising or consisting of nucleotide sequences having at least 70%, preferably at least 80%, more preferably at least 90%, still more preferably at least 95%, or most preferably 100% sequence homology to SEQ ID No 1 or 3.

Expression vectors may be selected depending on the host cell into which the polynucleotides of the invention may be inserted. Such transformation of the host cell involves conventional techniques such as those taught in Sambrook et al [Sambrook, J., Russell, D. (2001) Molecular Cloning: A Laboratory Manual, Cold Spring Harbor Laboratory Press, NY, USA]. Selection of suitable vectors is within the skills of the person knowledgeable in the field. Suitable vectors include plasmids, bacteriophages, cosmids, and viruses.

The hybrid proteins produced may be isolated and purified from the host cell by any suitable method e.g. precipitation or chromatographic separation e.g. affinity chromatography.

The invention also relates to the clinical uses of these chimeric polypeptides and to specific immunotherapy for the treatment of allergy, particularly allergy to the dust mite, *D. pteronyssinus*. As noted above, specific immunotherapy is a method of treating and preventing allergy by the administration of an effective quantity of one or more of the hydrid proteins of the present invention. Preferably the treatment is of mammals, particularly humans. Allergy may manifest itself as rhinitis, conjunctivitis, asthma, urticaria, angioedema, eczema, dermatitis, and/or anaphylactic shock. Accordingly, treatment and preventative therapy covered by the present application may include treatment of one or more of these conditions.

The hybrid proteins as prepared by the described process can be formulated as a medicament for the treatment of an allergic reaction. The invention also relates to possible compositions comprising these hybrid proteins as well as different ways of administering them. A particular embodiment of the invention relates to a vaccine composition. The main component is the hybrid protein which is preferably administered together with an adjuvant. There are several adjuvants suitable for the application to humans e.g. aluminium hydroxide. Preparation of vaccines is described in Vaccine Design ("The subunit and adjuvant approach"), eds. M F Powell & M J Newman, Plenum Press, New York, 1995.

The preferred forms of administration include all the standard administration methods described and suggested for vaccination in general and allergy immunotherapy in particular (in oral, sublingual, transdermal, intravenous, intranasal, mucous form, etc.).

The hypoallergenic properties of the hybrid proteins of the present invention are discussed below. The immunological tests carried out by the inventors using ELISA and ELISA inhibition experiments indicate that the QM2 chimera showed no IgE recognition in sera of patients allergic to *D. pteronyssinus* (FIG. 9). Despite containing the majority of the sequences of both allergen proteins, the chimera QM1 has an IgE binding capacity 2500 times lower than that of the mixture of both natural proteins, as shown in FIG. 10. QM1 contains the majority of the sequences of both proteins but has mutations in two cysteines of Der p 2 (residues 8 and 119).

These low allergenicity data were authenticated by in vivo experiments on 107 patients using skin prick tests. The allergenicity (IgE binding capacity as indicated by, for example the wheal size) of the chimera QM1 was around 50 times lower than that obtained with the two isolated natural proteins (FIG. 11). The allergenicity of QM2 was practically zero.

The low allergenicity of the chimera QM2 was corroborated when the reactivity of this molecule was measured with sera from 107 patients allergic to *D. pteronyssinus* (FIG. 12). This reduction in allergenicity was accompanied by maintenance of the immunogenic capacity of the chimeras QM1 and QM2, which was surprisingly higher than that observed for the sum of the individual natural proteins (FIG. 13 and FIG. 14A). These characteristics allow these chimeras to be used as substitutes for the complete allergenic extract of the prior art, but with greater safety.

Deposit of Strains

A strain of the microorganism according to the present invention has been deposited in the Colección Española de Cultivos Tipo (CECT) of the University of Valencia (Universidad de Valencia, Edificio de Investigación, Campus de Burjasot, 46100 BURJASOT, Valencia) in accordance with the Treaty of Budapest on the International Recognition of the Deposit of Microorganisms for the Purposes of Patent Procedure, with the following references:

| CECT 7317 | *Escherichia coli* QM1 |
|---|---|
| CECT 7318 | *Escherichia coli* QM2 |

Deposited on 3 Oct. 2007.

DESCRIPTION OF THE DRAWINGS

FIG. 1 shows sequences of nucleotides and amino acids deduced from the foregoing corresponding to the pre-protein proper p 1, in which the pre-region has been framed and the disulphide bridges are indicated by lines connecting the relevant encircled cysteine residues.

FIG. 2 shows sequences of nucleotides and amino acids deduced from the foregoing corresponding to the mature protein Der p 2, in which the disulphide bridges are indicated by lines connecting the relevant encircled cysteine residues.

FIG. 4 shows sequences of amino acids and nucleotides of QM1. The introduced residues of Der p 2 are shaded and those of Der p 1 are framed. The substituted residues are shown by a double frame.

FIG. 6 shows sequences of QM2 amino acids and nucleotides. The introduced residues of Der p 2 are shaded and those of Der p 1 are framed. The residues substituted during construction of the chimera are shown by a double underscore.

DETAILED DESCRIPTION

Figure 13:
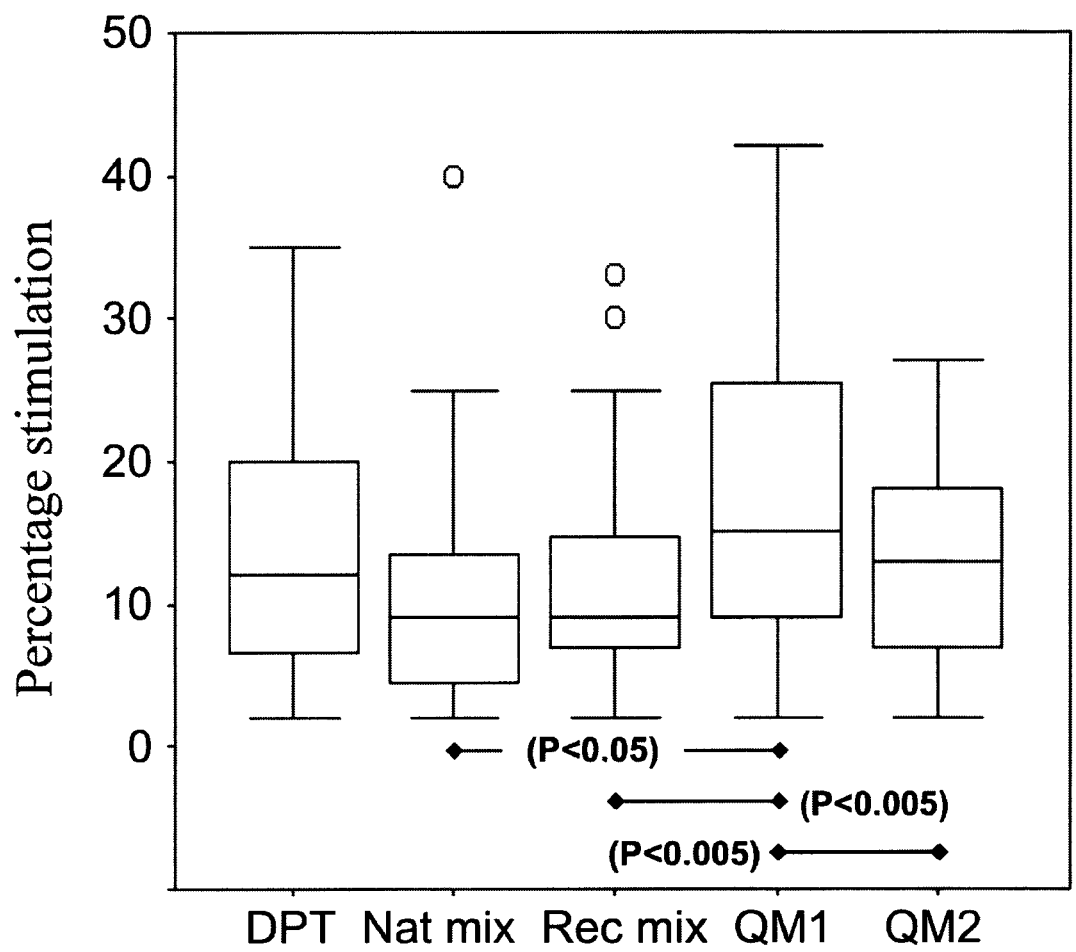
FIG. 13 shows the proliferation of T lymphocytes obtained with 10 μg/ml of the extract of *D. pteronyssinus* (DPT), the two hybrid proteins and the equimolecular mixtures of the natural and recombinant forms of Der p 1 and Der p 2 (NAT MIX and REC MIX, respectively). The value shown is that of the stimulation index (%). The values of P are only shown when the differences are significant.
Figure 14:
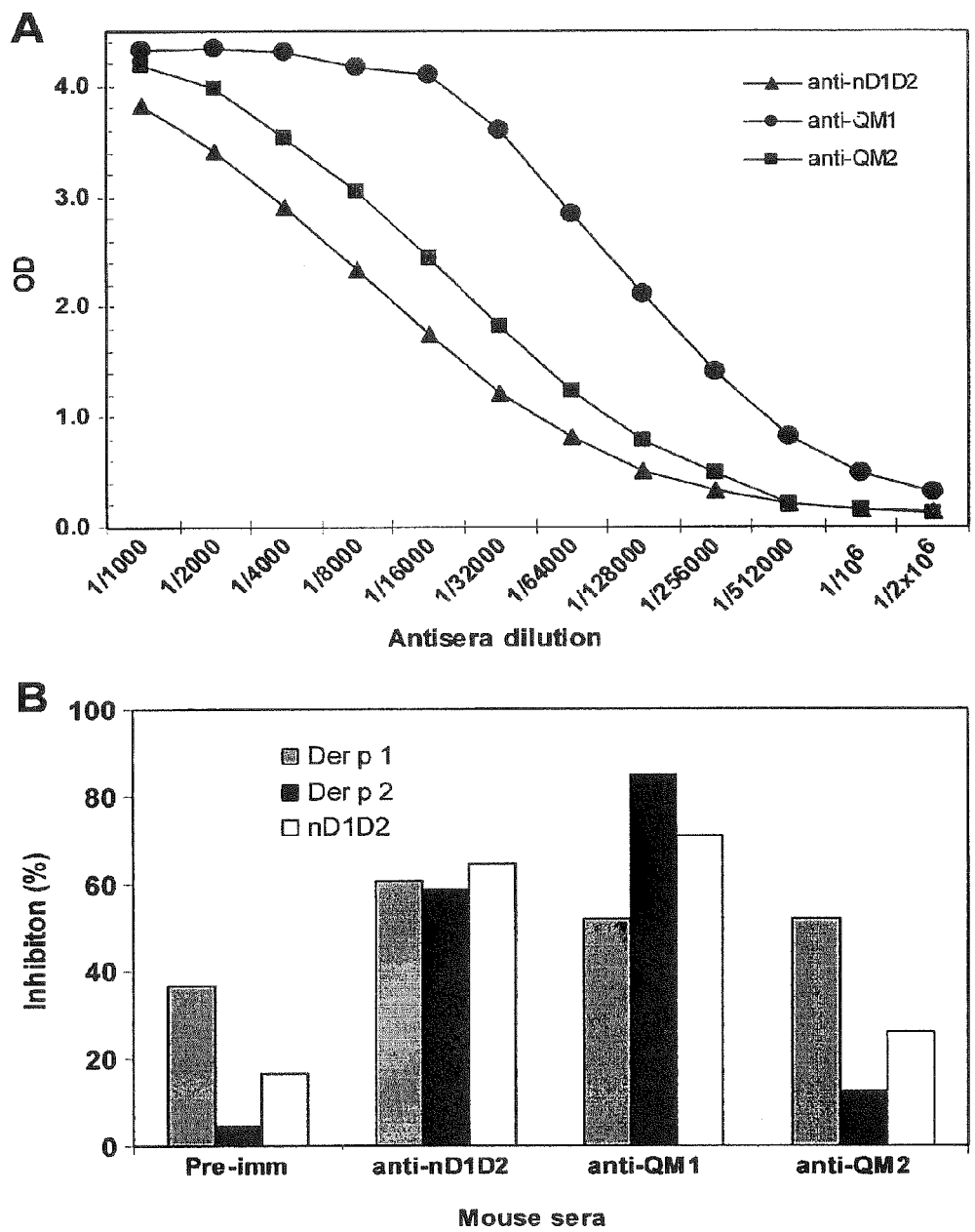
FIG. 14: (A) Titration of antisera raised by immunization of mice with nD1D2, QM1, and QM2. Different dilutions of antisera were tested for reactivity to the natural equimolar mix of nDer p 1 and nDer p 2 (nD1D2). The mean optical density (OD) corresponding to bound IgG antibodies are displayed for each serum dilution. (B) Inhibition of human IgE binding to nD1D2 and its components, Der p 1 and Der p 2 after pre-incubation with nD1D2-, QM1-, and QM2-specific mouse IgG antibodies.

The low allergenicity hybrid proteins according to the present invention are obtained, in the case of QM1, by the fusion of both proteins (Der p 1 and Der p 2) and the elimination of one of the disulphide bridge (residues 8-119) and, in the case of QM2, by the insertion of the protein Der p 1 between the residues 73 and 74 of Der p 2. Surprisingly, despite these changes the hybrid proteins (QM1 and QM2) exhibited higher T-cell stimulating capacity (FIG. 13) and induced stronger immunogenicity than the separated wild-type molecules (FIG. 14A).

The peptide fragments making up the hybrid proteins can be synthesised from nucleotide sequences encoding them by a qualified and trained person by e.g. polymerase chain reaction (PCR) amplification according to methods well known in the art such as those described e.g. in Sambrook et al [Sambrook. J., Russell, D. (2001) Molecular Cloning: A Laboratory Manual, Cold Spring Harbor Laboratory Press, NY, USA]. Said nucleotide sequences, having been digested by suitable restriction enzymes, can be incorporated in an expression vector by ligation. The different nucleotide sequences encoding the peptide fragments are bound using linkers formed with sequences recognised by different restriction enzymes, and some residues therefore appear in the final hybrid peptide molecule that did not exist in the original sequence of the natural allergen. These new residues did not interfere with the correct translation of the protein and have been marked in the sequence in FIG. 6 by a double underscore.

The present invention covers the use of the chimeras according to the present invention, QM1 and QM2, or synthetic peptides derived there from for desensitisation treatments in animals, particularly mammals such as humans. Desensitisation methods involve the repeated administration by parenteral (subcutaneous, intravenous or intramuscular), oral, sublingual, nasal or rectal route. These hybrid proteins may be administered alone or in combination with pharmaceutically excipients, adjuvants and/or and diluents, according to the current legislation and the applicable galenical procedures.

The immunological characteristics of the hybrid proteins according to the present invention are set out below.

Figure 9:
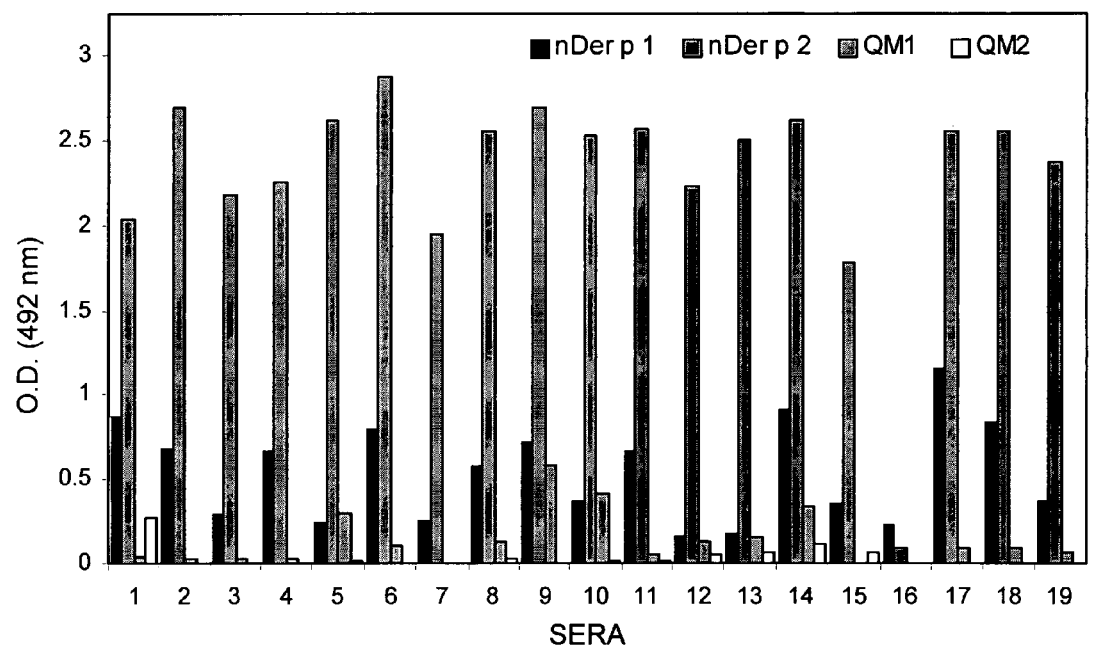
FIG. 9 shows the binding of IgE antibodies to nDer p 1, nDer p 2, QM1 and QM2 using sera from 19 patients allergic to *D. pteronyssinus* (dilution 1/4).
Figure 10:
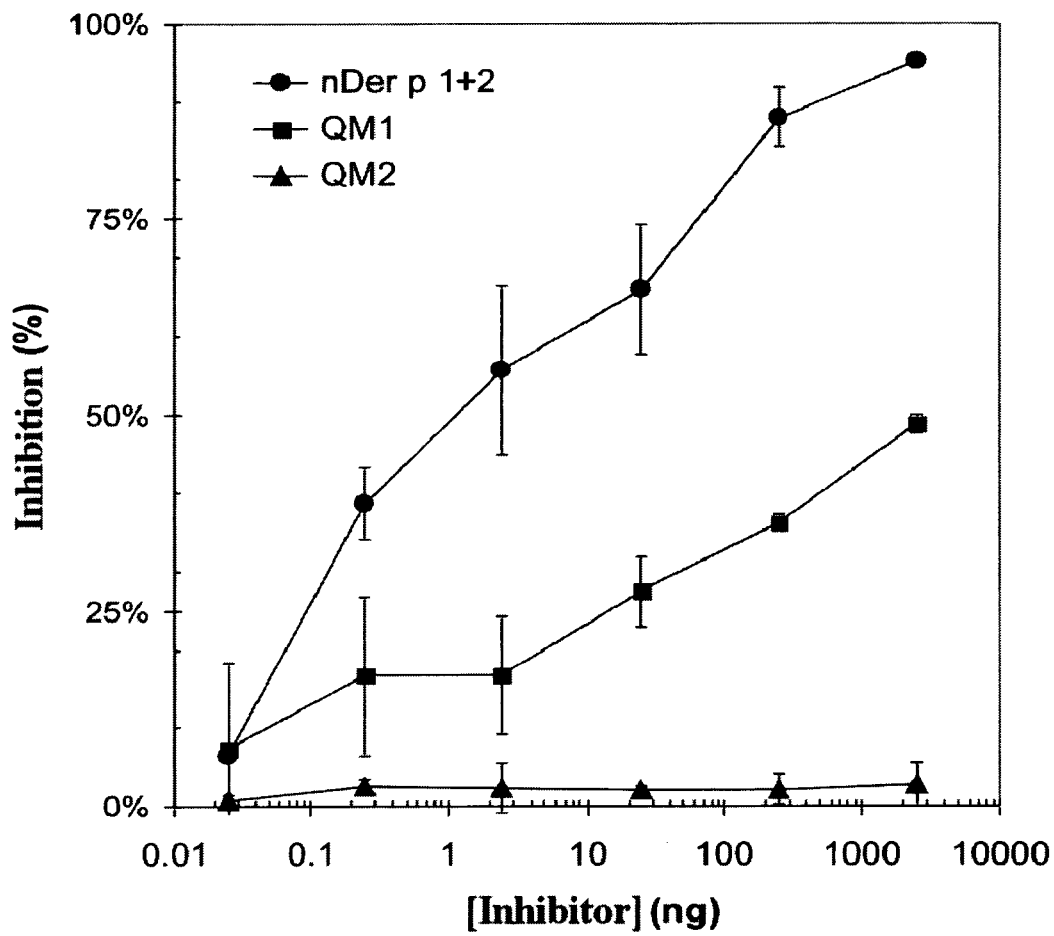
FIG. 10 shows results from an ELISA inhibition test of IgE binding activity of a pool of sera from patients allergic to *D. pteronyssinus* to an equimolecular mixture of nDer p 1+Der p 2 in the solid phase. The inhibitor molecules used were: nDer p 1+Der p 2, QM1, and QM2. Each value corresponds to the average inhibition obtained from three experiments with a standard deviation of less than 10%.
Figure 11:
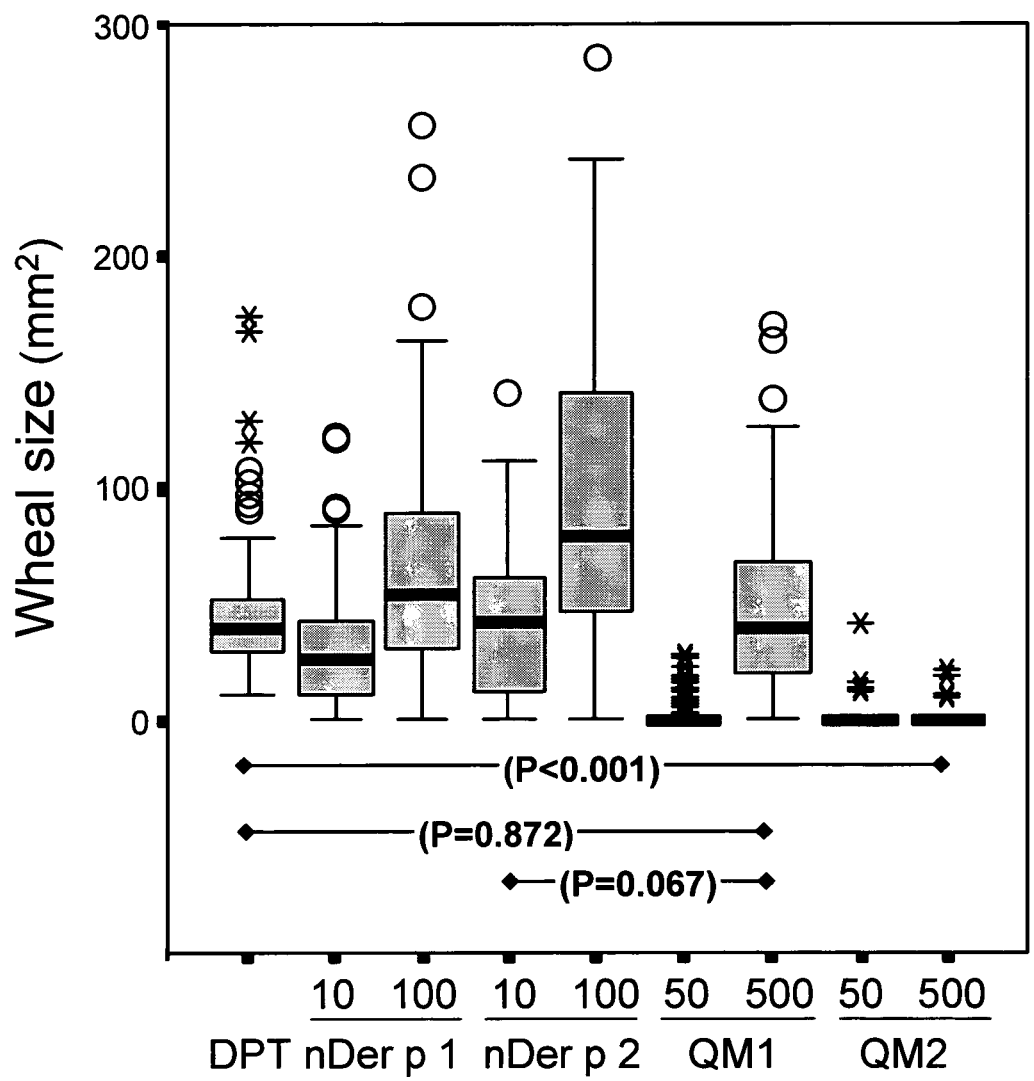
FIG. 11 shows the result of skin tests from individual patients (n=107) with an extract of *D. pteronyssinus* (DPT), nDer p 1 and nDer p 2 (both at 10 and 100 μg/mL), and QM1 and QM2 (both at 50 and 500 μg/mL) are shown. Individual values, in mm$^2$, are given as means of duplicate wheal surface areas measured on both arms. The results are shown as box-plots where the edges of each box mark the 25$^{th}$ and 75$^{th}$ percentiles and the lines indicate the median values. The bars extending up and down from each box show the largest observed value that is not an outlier. Open circles and stars indicate outliers and extremes of each patient group. P values after Wilcoxon ranks test analysis are included.

The QM1 and QM2 hybrid proteins described in the invention are hypoallergenic: as shown in FIGS. 8, 9, 10 and 12. They have lower reactivity to the serum of patients allergic to *D. pteronyssinus* than the complete extract or the combined natural proteins, and, particularly for the QM2 chimera, lower capacity to activate basophils in "ex vivo" tests. This hypoallergenicity has also been demonstrated in in vivo skin tests (FIG. 11).

Figure 8:
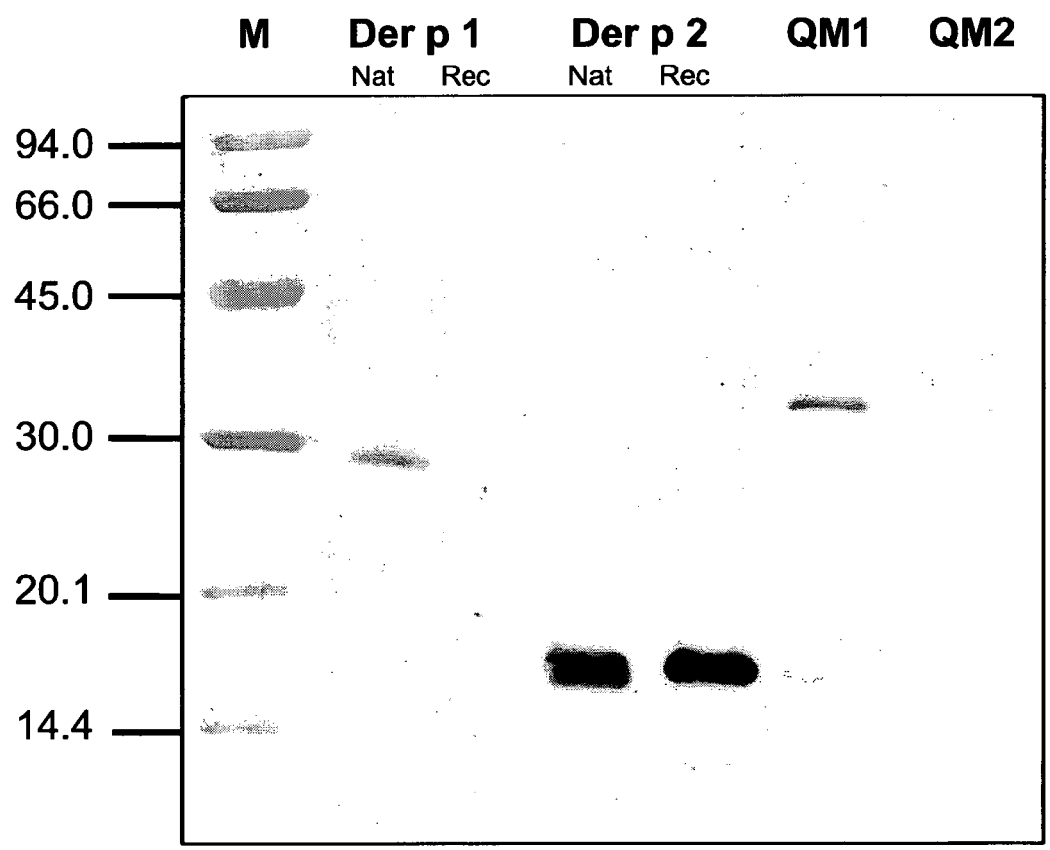
FIG. 8 shows immunoblot incubated with IgE antibodies of a pool of sera from patients allergic to *D. pteronyssinus* in which the natural and recombinant allergens (Der p 1 and Der p 2) and the QM1 and QM2 fusions appear. Lane M indicates standard molecular weight markers.

FIG. 8 shows an immunodetection test which indicates that the chimeras QM1 and QM2 have lower IgE-binding capacity in allergic patients compared with the reactivity of the natural protein Der p 2. This reduction in allergenicity was quantified by means of ELISA-inhibition with a mixture of sera of patients allergic to *D. pteronyssinus* (FIG. 10). 2500 times as much of the QM1 protein was required to achieve 50% inhibition than of the mixture of the two natural proteins. It can therefore be inferred that it was 2500 times less allergenic than the natural proteins, which would indicate a reduction in IgE-binding capacity to the mixture of the two natural proteins of more than 99%.

A more direct measure of the hypoallergenicity of the chimeras QM1 and QM2 was obtained by direct measurements of skin reactivity in 107 patients allergic to *D. pteronyssinus*. The data in FIG. 11 show that the chimera QM2 had markedly reduced skin reactivity. Chimera QM2 on the other hand only produced positive reactivity in 5 patients. A comparison of each distribution shows that the chimera QM1 has a mean wheal size 50 times lower than that observed for nDer p 2 and 10 times lower than that observed for nDer p 1, which would indicate a reduction in allergenic activity of 90-98%. This was despite the higher dosages used for the hybrid proteins.

Figure 12:
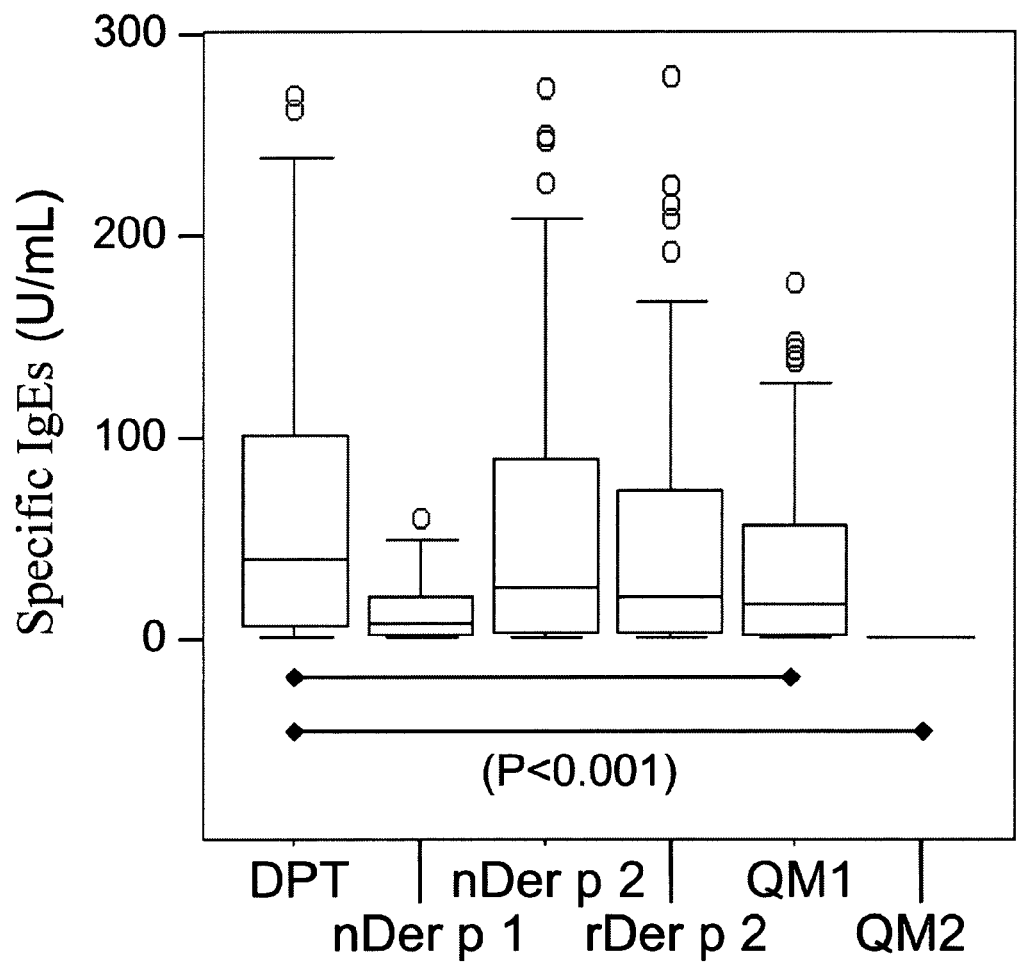
FIG. 12 shows a box-plot representation of duplicate specific IgE means from individual patient sera (n=107) to an extract of *D. pteronyssinus* (DPT), nDer p 1, nDer p 2, nD1D2, QM1, and QM2. The results are shown as box-plots where the edges of each box mark the 25$^{th}$ and 75$^{th}$ percentiles and the lines indicate the median values. The bars extending up and down from each box show the largest observed value that is not an outlier. Open circles and stars indicate outliers and extremes of each patient group. P values after Wilcoxon ranks test analysis are included.

The low IgE binding capacity of the hybrid protein QM2 was also demonstrated with the serum of 107 other patients allergic to *D. pteronyssinus* measured by EAST (FIG. 12). In all patients IgE binding was practically non-existent for QM2 compared to the mixture of natural proteins, DPT, and to the single proteins in either recombinant or national form.

This large reduction in the capacity to bind IgE and cause adverse reactions was accompanied by maintenance of immunogenic capacity. The proteins QM1 and QM2 showed a lymphoproliferation index similar to that induced by the mixture of the two pure proteins, Der p 1 and Der p 2 in combination (in both the natural and recombinant forms) as shown in FIG. 13. This demonstrates that the hybrid proteins QM1, constructed as a fusion of the mutated polypeptide Der p 2 (C8-C119) and Der p 1, and QM2, constructed with 2 fragments of Der p 2 and Der p 1, contain fewer conformational IgE-binding epitopes but maintained sufficient T epitopes to induce a protective immune response.

Another desirable feature of hypoallergenic molecules when used as candidates for SIT, apart from having a reduced IgE-binding activity when compared to the corresponding allergens and containing T-cell epitopes, is that they should have the capacity to induce 'blocking' antibodies that prevent the degranulation and release of histamine. Immunization of mice with the hybrid proteins QM1 and QM2 induced stronger IgG response than the mixture of wildtype proteins. These Der p 1 and Der p 2-specific IgG antibodies inhibited the binding of house dust-mite allergic patients' IgE to the natural allergens, further improving prevention of allergic symptoms.

The invention will be better understood from the following examples relating to the experimental stages to prepare the invention and demonstrate its qualities. These examples are simply illustrative and not limiting to the invention.

EXAMPLES

Example 1

Purification of the Natural Allergens Der p 1 and Der p 2 from Mite Bodies

A mixture of lyophilised bodies and faeces of *D. pteronyssus* (Laboratorios Leti, Madrid, Spain) was used as the starting material, extracted with 10 volumes (p/v) of PBS (phosphate buffered saline) supplemented with 1 mm of PMSF (phenylmethylsulfonyl fluoride) for 15 minutes with rapid stirring at 4° C. It was then centrifuged at 3,800×g for 15 minutes at 4° C. The extraction supernatant was filtered through AP (Millipore) and 60% of ammonium sulphate 361 g/l) was added slowly for 30 min. After stirring for 1 hour at 4° C. it was centrifuged for 15 minutes at 17,000×g and 4° C.

Purification of Natural Der p 1

The pellet obtained after centrifugation was resuspended in 2 ml of 20 mM Tris pH 8.0 and filtered through 0.22 Molecular-sieve chromatography was carried out in a Superdex S200 16/60 column (GE-Healthcare, Uppsala, Sweden) for which the column was equilibrated with PBS and the 2 ml from the previous step were injected. 3 ml fractions were collected from the exclusion volume which were analysed by SDS-PAGE in non-reducing conditions, being combined with 24 kDa fractions. Next anion-exchange chromatography was carried out in a HighTrap Q column (GE-Healthcare) for which the column was equilibrated with 20 mM Tris pH 8.5. The positive fractions from the previous step were dialysed against 5 l of distilled water for 120 min, and taken to 20 mM Tris pH 8.5. The sample was injected at 1 ml/minute and eluted with a gradient of 200-1000 mM NaCl in 20 mM Tris pH 8.5. The unbound fraction was collected.

The purity of the preparation was checked by electrophoresis in polyacrylamide gels with SDS (SDS-PAGE). Basically the technique described by Laemmli was followed [(19) Laemmli, U. K. (1970). Cleavage of structural proteins during the assembly of the head of bacteriophage $T_4$. Nature 277, 680-685], using a MINI-PROTEAN (Bio-Rad) electrophoresis appliance. The gels, measuring 10×10 cm and with a polyacrylamide concentration of 12.5%, were subjected to a 200-volt current for 45 minutes in Tris-Glycine buffer. The proteins used as markers were those of the Bio-Rad kit for low molecular weights. Calculation of molecular weights and densitometric analysis of the gels were performed using an image analyser (Diversity, BioRad).

Figure 7:
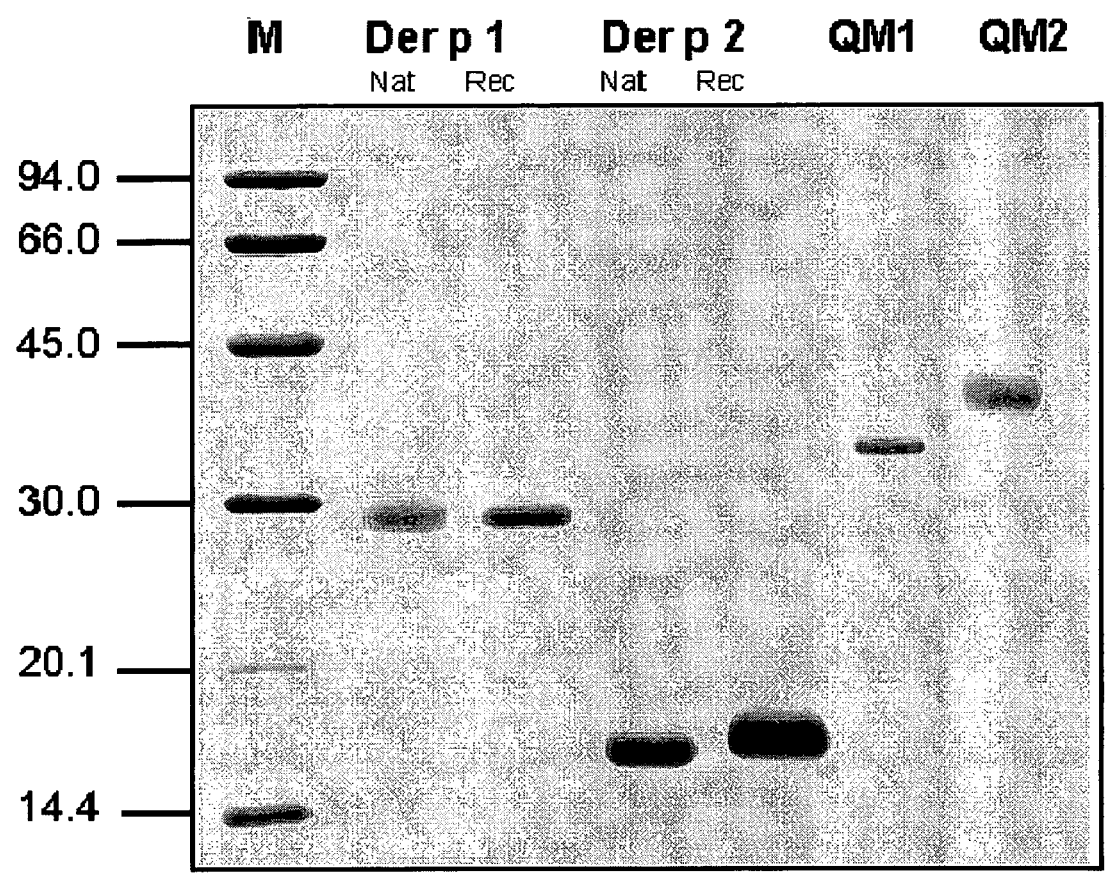
FIG. 7 shows a Coomassie Blue-stained polyacrylamide gel after electrophoresis in which the natural and recombinant allergens (Der p 1 and Der p 2) and the QM1 and QM2 fusions appear.

The result of the purification of natural Der p 1 was a protein with a purity of more than 98% and a size of 29.07 kDa when the SDS-PAGE was carried out in reducing conditions (FIG. 7).

Purification of Natural Der p 2

239 g/l of ammonium sulphate was added to the precipitation supernatant with 60% ammonium sulphate to obtain a concentration of 95% and left overnight being stirred at 4° C. It was centrifuged for 15 minutes at 17,000×g and 4° C., and the pellet was resuspended in 25 ml of MilliQ water. Next anion-exchange chromatography was carried out in a High-Flow Q 16/20 column (GE-Healthcare) equilibrated with 50 mM Tris pH 8.0. The sample was dialysed against 5 l of water overnight with three changes of water and taken to 50 mM Tris pH 8.0. The sample was injected at 5 ml/minute and the unbound fraction was collected. The third purification step consisted of cation-exchange chromatography in a HighTrap SP column (GE-Healthcare) equilibrated with 20 mM AcNa pH 5.5. The unbound fraction from the previous step was dialysed against 5 l of water for 3 hours and taken to 20 mM AcNa pH 5.5. The sample had a flow rate of 1 ml/minute and was eluted with a gradient of 200-1000 mM NaCl in 20 mM AcNa pH 5.5. As the final purification step, molecular-sieve chromatograhy was performed in a Superdex S75/300 column (GE-Healthcare) equilibrated with PBS. The fraction from the previous step eluted with 200 mM NaCl was concentrated in Amicon Ultra 4 (Millipore) and had a flow rate of 0.4 ml/min, and fractions of 0.5 ml were collected. The fractions were analysed using SDS-PAGE. Those that contained a 16 kDa protein corresponding to Der p 2 were combined together.

The purification of natural Der p 2 resulted in a protein with a purity of over 95% and a size of 16.63 kDa when the SDS-PAGE was performed in reducing conditions (FIG. 7).

Example 2

Cloning of the Der p 1 and Der p 2 Allergens

The complementary DNA (cDNA) coded for the allergens Der p 1 and Der p 2 was cloned by reverse transcription followed by PCR amplification using mRNA as a template isolated from *Dermatophagoides* and specific primers in each case. The mRNA was isolated from 100 mg of *D. pteronyssinus* bodies (Laboratiorios Leti, Madrid, Spain) using the Quick Prep MicroRNA Purification Kit (GE-Healthcare). The cDNA was obtained by reverse transcription of the mRNA using the First-Strand cDNA Synthesis Kit (GE-Healthcare).

The primers consisted of the hybridisation zone, various cleavage sites for different restriction endonucleases (underlined below), and anchoring nucleotides. The PCR amplification reaction had the following components in a reaction volume of 50 µl: amplification buffer ×10, 5 µl; 200 µm of dNTPs; 100 pm of each oligonucleotide primer; 2.5 units of Taq polymerase (Pfx DNA polimerase, Invitrogen); 1 ng DNA template and sterile distilled water up to 50 µl. The amplification reaction was carried out in a RoboCycler thermocycler (Stratagene) under specific conditions which were described in each case. The product of the reaction was subjected to electrophoresis in agarose gels (2%) and the band of interest was isolated from the gel by Geneclean (Bio101), using the protocol described by the manufacturer. The fragments isolated were ligated into the pGEM vector (Promega). The ligation mixture was used to transform competent cells of *E. coli* DH5α (obtainable through Invitrogen, Paisley, United Kingdom). The resulting colonies were grown to isolate their plasmid DNA, which was digested with suitable enzymes to release the fragment of interest. The positive clones were selected for their sequencing. The DNA inserted into pBluescript was sequenced by the Sanger method modified for use with fluorescent dideoxynucleotides and amplified in the thermocycler using the PRISM Ready Reaction DyeDeoxy Termination Cycle Sequencing Kit, (Perkin Elmer) following the instructions of the manufacturer.

cDNA of Der p 1

The region of cDNA coding for Der p 1 was amplified by PCR using primers designed according to published sequences (GenBank access number: P08176). The direct primer 5'-ACTGAC AGGCCTCGTCCATCATCGATCAAAAC-3' included the cleavage sequence of the enzyme StuI (underlined) and the reverse primer 5'-CG GAATTCCTAGGTTAGAGAATGACAACATATGG-3' included the cleavage zones of the EcoRI (underlined) and AvrII (italic) endonucleases. The amplification conditions were: 94° C.-1' (1 cycle); 94° C.-30", 48° C.-1', 72° C.-1' (35 cycles); 72° C.-10' (1 cycle). The PCR product obtained was isolated, cloned in the pGEM (Promega) vector and sequenced.

The plasmid DNA of Der p 1 coded a protein of 302 amino acids which included a preprotein of 80 and a mature protein of 222 amino acids (FIG. 1). This sequence showed a difference ($His^{152} \rightarrow Asn$) compared with the sequence described for Der p 1.0105 (P08176). The calculated molecular weight of the protein was 24.97 kDa with an isoelectric point of 5.49.

cDNA of Der p 2

The cDNA region coding for Der p 2 was amplified by PCR using primers designed according to published sequences (AAF86462). 5'-C GGGATCCGATCAAGTCGATGTCAAAG-3' was used as a direct primer, which included the cleavage sequence of the restriction enzyme BamHI and 5'-CG GAATTCTTAATCGCGGATTTTAGC-3' as the reverse primer with the cleavage sequence of the restriction enzyme EcoRI. The amplification conditions were: 94° C.-1' (1 cycle); 94° C.-30", 48° C.-1', 72° C.-1" (35 cycles); 72° C.-10' (1 cycle). The PCR product obtained was isolated, cloned in the pBluescript II KS vector (Stratagene) and sequenced. The plasmid DNA that coded Der p 2 was isolated after digestion with the restriction enzymes BamHI/EcoRI and subcloned in the pKN172 vectors [(20) Way, M., Pope, B., Gooch, J., Hawkins, M., Weeds, A. G. (1990) Identification of a region in segment 1 of gelsolin critical for actin binding. EMBO J. 9; 4103-4109] and pTrcHis A (Invitrogen, Carlsbad, Calif., USA)].

The Der p 2 sequence obtained coded for a polypeptide of 129 amino acids (FIG. 2) which included an amino acidic change (Leu$^{127}$→Ile) with respect to the Der p 2.0102 (AAF86462) sequence. However Der p 2 (P49278) and other isoforms described also had an isoleucine in this position. The protein had a theoretical molecular weight of 14.106 kDa and an isoelectric point of 7.10.

Example 3

Expression and Purification of Recombinant Der p 2

The *E. coli* BL21 (DE3) cells transformed with the corresponding plasmid by the Hanahan method [(21) Hanahan, D. (1983). Studies on transformation of *Escherichia coli* with plasmids. J. Mol. Biol. 166, 557-580] were spread on the Petri plates containing LB medium supplemented with 200 µg/ml of ampicillin. From a cell colony, 50 ml of the same medium was preinoculated, and incubated overnight at 37° C. with stirring (260 rpm). 1 liter of the same medium was inoculated with said preinoculation starting from an optical density (600 nm) of 0.2. It was incubated at 37° C. with stirring until an optical density (600 nm) of 0.6 was achieved (approx. 90 minutes), at which time induction was carried out with isopropyl-thio-β-galactoside (IPTG) at a final concentration of 0.6 mM. After an induction period of 3 hours the cells were collected by centrifugation.

The cells were centrifuged at 10000 rpm for 15 minutes at 4° C. and resuspended in 50 ml of lysis buffer (50 mM Tris pH 8.0; 1 mM DTT (dithiothreitol)). The resuspension was treated with lysozyme (0.1 mg/ml of final concentration) for 30 minutes at 37° C. with stirring. Next it was sonicated in an ice bath for 5 minutes, 1% Triton X-100 was added and it was left to incubate for 30 minutes at ambient temperature with gentle stirring. After being centrifuged at 8000×g for 15 minutes the pellet was resuspended in 20 ml of 2 M urea and 0.2% Triton X-100 and incubated for 30 minutes at ambient temperature with gentle stirring. It was sonicated in an ice bath for 1 minute and centrifuged at 8000×g and 4° C. for 15 minutes. The pellet was resuspended in 10 ml of 6 M guanidine chloride and 0.5% β-mercaptoethanol. It was maintained in magnetic stirring for 1 hour at 4° C. and dialysed overnight against 200 ml of 6 M urea in 25 mM Tris pH 8.0. To improve the folding thereof the sample was then diluted to 1-2 mg/ml with 6 M urea and dialysis was performed step by step at 4° C. against: 400 ml of 3 M urea/1 1.5 M urea/0.75 M urea/0.37 M urea/0.18 M urea making the changes every 90 minutes. Finally it was left to dialyse overnight at 4° C. against 5 l distilled water. Purification ended with anion-exchange chromatography in a HighFlow SP 16/20 column (Healthcare) equilibrated with 25 mM AcNa pH 5.5. The sample was taken to 25 mM AcNa pH 5.5 and after centrifuging at 3800×g for 10 minutes and filtering through AP (Millipore) and 0.45 µm (Millipore) filters it was passed through the column at 5 ml/min. Elution was carried out with 1000 mM NaCl in 25 mM AcNa pH 5.5.

The yield from purification was 3.8 mg per liter of culture. Purification of recombinant Der p 2 resulted in a protein with a purity of over 95% and a size of 17.05 kDa when the SDS-PAGE was carried out in reducing conditions (FIG. 7).

Example 4

Construction of the QM1 Fusion

This began with the plasmid DNA of Der p 2 which was amplified by PCR with the primer 5'-CG<u>GGATCC</u>GTCAAAGATAGTGCCAATC-3' and 5'-ACG-GAT<u>CTGCAG</u>GTAGCAATAGCACTGGCCAA-3, which included the cleavage sequences of the enzymes BamHI and PstI, respectively (underlined). The amplification conditions were: 94° C.-1' (1 cycle); 94° C.-30", 56° C.-30", 72° C.-1' (35 cycles); 72° C.-10' (1 cycle). The fragment obtained was ligated into pBluescript KS vector (Stratagene) cleaved with BamHI/PstI and sequenced. This construction was digested with PstI/EcoRI, and a partial sequence of the mature protein of Der p 1 which had been obtained after digesting the initial sequence with the same enzymes PstI/EcoRI was incorporated by ligation. The fusion protein obtained was subcloned in BamHI/EcoRI in the expression vectors pKN172 and pTrcHis.

Figure 3:
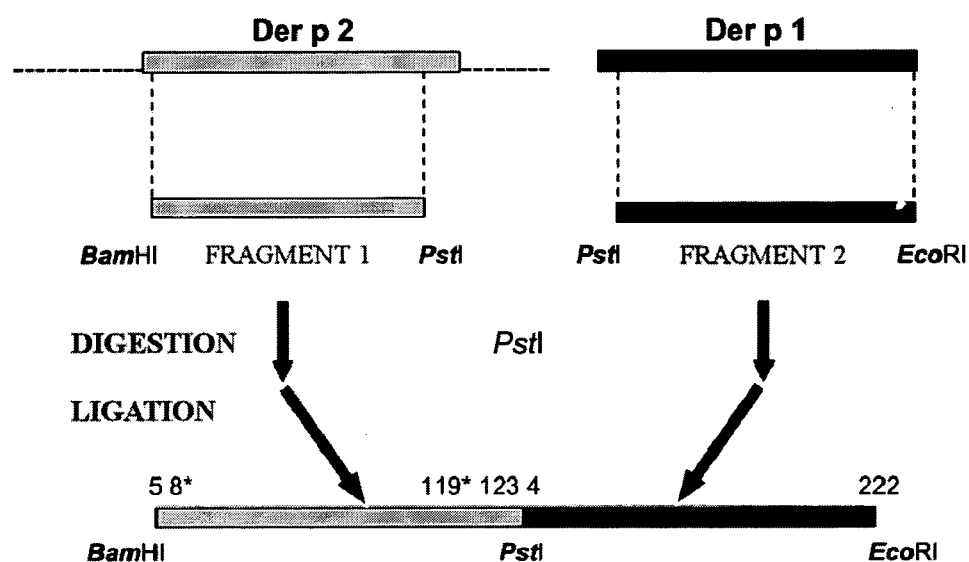
FIG. 3 shows a QM1 construction diagram. The * indicates the location of substituted residues.

The fusion protein 1 resulted from the binding of two fragments (FIG. 3). The first fragment was formed by the sequence coded from the amino acid 5 to 123 of Der p 2. The oligonucleotides designed for reamplification of this sequence included base changes which involved the replacement of the cysteines of positions 8 and 119 of the original protein by serines. The second fragment coded from amino acid 4 to 222 of the mature protein of Der p 1. The second fragment was bound to the first by the core of the enzyme PstI located between amino acids 3 and 5 of the mature protein of Der p 1. The resulting plasmid DNA coded a protein of 338 amino acids (FIG. 4) with a molecular weight of 37.56 kDa and a theoretical isoelectric point of 6.16.

Example 5

Construction of the QM2 Fusion

The fusion protein 2 was constructed by the binding of three fragments:

Fragment 1, corresponding to the N-terminal end of Der p 2, was amplified with the direct primer 5'-CG<u>GGATCC</u>GATCAAGTCGATGTCAAAG-3' which included the core of the enzyme BamHI and with the reverse primer 5'-CC<u>GAATTC</u>CCTAGG CTGCAGCCATTTGGATCGAT-3' which included the cores of EcoRI, AvrII and PstI. The amplification conditions were: 94° C.-1' (1 cycle); 94° C.-30", 56° C.-30", 72° C.-1' (35 cycles); 72° C.-10' (1 cycle).

Fragment 2 of Der p 1 was amplified with the following oligonucleotides: 5'-ACTGAC<u>AGGCCT</u>CGTCCATCATCGATCAAAAC-3' and 5'-CA<u>CCTAGG</u>GAGAATGACAACATATGG-3'. The direct primer included the cleavage sequence of StuI and the reverse primer included that of AvrII. The amplification conditions were: 94° C.-1' (1 cycle); 94° C.-30", 56° C.-30", 72° C.-1" (35 cycles); 72° C.-10' (1 cycle).

Fragment 3 was obtained by PCR using Der p 2 as a template and the primers 5'-CA<u>CCTAGG</u>CATTACATGAAAAGCCCA-3' and 5'-CG<u>GAATTC</u>TTAATCGCGGATTTTAGC-3' which had the recognition sequences for the enzymes AvrII and EcoRI, respectively. The amplification conditions were: 94° C.-1' (1 cycle); 94° C.-30", 52° C.-30", 72° C.-1' (35 cycles); 72° C., 10' (1 cycle). Isolation of the desired fragment and reamplification in the following conditions: 94° C.-1' (1 cycle); 94° C.-30", 56° C.-30", 72° C.-1' (35 cycles); 72° C.-10' (1 cycle). Fragment 1 was cloned in the pBluescript KS vector (Stratagene) in BamHI/EcoRI. This first construction was digested with PstI and AvrII and fragment 2 previously digested with the same enzymes was incorporated by ligation. Digestion with PstI ensured that this second fragment only included a partial sequence of the mature protein of Der p 1. The new construction which included fragments 1 and 2 was in turn digested with AvrII and EcoRI and bound to fragment 3. The plasmid DNA that coded the fusion protein was sequenced, and subcloned in the pKN172 and pTrcHis A vectors for expression thereof.

Figure 5:
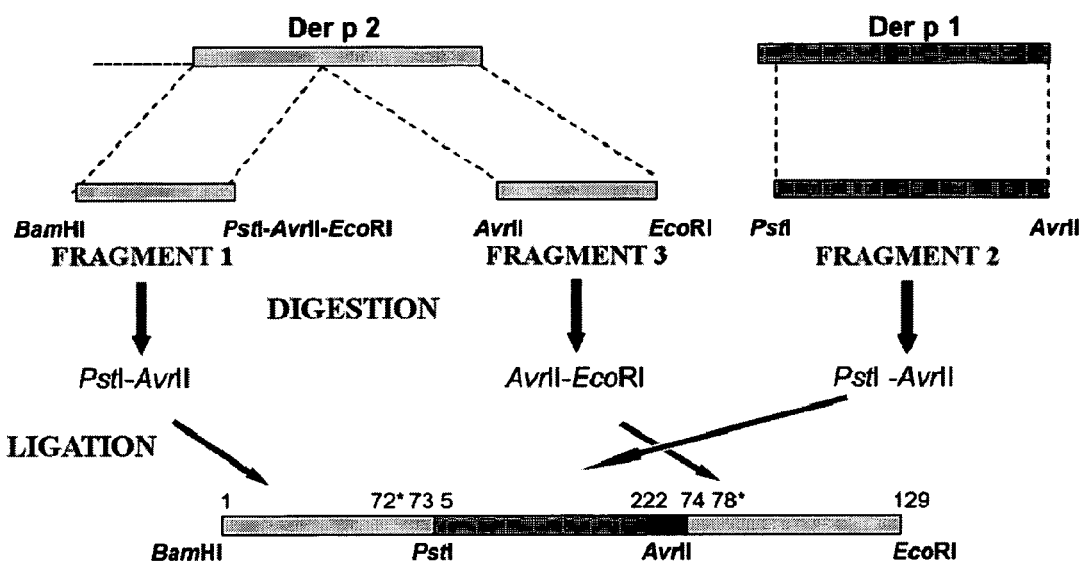
FIG. 5 shows a QM2 construction diagram. The * indicates the location of substituted residues.

The DNA of the QM2 fusion was formed from the sequence that coded the complete protein of Der p 2, into which had been inserted between the bases that determined the amino acids 73 and 74 a sequence that coded from the amino acid 5 to the final residue of the mature protein of Der p 1 (FIG. 5). The binding of Der p 1 with the second fragment of Der p 2 involved the inclusion of 6 additional bases of the core of AvrII and which coded for proline and arginine. The primers designed for the construction of fragments 1 and 3 included some differences with respect to the original sequence: changes in the amino acids 72 (Ala→Gly) and 78 (Cys→Ser) of Der p 2 (FIG. 6). The amino acid 342 of the protein turned out to be a valine instead of the alanine of the original sequence of Der p 2. The final protein completely destroyed the three-dimensional structure of Der p 2 when the sequence of Der p 1 was introduced in its amino acid 73. The final hybrid protein was made up of 349 amino acids with a calculated molecular weight 38.92 kDa and a theoretical isoelectric point of 6.22.

Example 6

Expression and Purification of the Hybrid Proteins QM1 and QM2

Starting with a colony of E. coli BL21 (DE3) cells transformed with the corresponding plasmid isolated from an LB plate supplemented with 200 µg/ml of ampicilin, a pre-inoculation of 50 ml of the same medium was carried and incubated overnight at 37° C. with stirring (260 rpm). 1 liter of the same medium was inoculated with said pre-inoculation starting with an optical density (600 nm) of 0.2. It was incubated at 37° C. with stirring until it reached an optical density (600 nm) of 0.6 (approx. 90 minutes), at which time induction with isopropyl-thio-β-galactoside (IPTG) at a final concentration of 0.6 mM was carried out. After an induction period of 3 hours the cells were collected by centrifugation.

QM1 Purification

The lysis conditions of the recombinant bacteria and refolding by dialysis in stages to eliminate the urea were as for the purification of rDer p 2 (Example 3). Finally oxidative folding by dialysis was carried out at 4° C. against 1 l of 5 mM cysteine/1 mM cystine in 50 mM Tris pH 8.0 overnight. Finally it was centrifuged at 3800×g and 4° C. for 10 minutes and the supernatant was filtered through AP (Millipore) and dialysed against 2 mM phosphate pH 8.5 for 2 hours and centrifuges at 18000×g for 15 minutes to remove possible precipitated material. The final yield from purification was 120 mg per liter of culture medium.

QM2 Purification

The lysis conditions of the recombinant bacteria were as for the purification of rDer p 2 (Example 3). 50 mM DTT was added to 135 mg of protein in 10 ml 6 M guanidine chloride and incubated for 1 hour at ambient temperature. Next 0.2 M 2-iodoacetamide was added and incubated for 1 hour at ambient temperature. Finally, 0.2 M β-mercaptoethanol was added, incubated for a further hour at ambient temperature and taken to 50 ml with 6 M urea. Next folding was carried out in stages by dialysis to eliminate the urea as for the purification of rDer p 2 (Example 3) and centrifuged at 3800×g for 15 minutes to remove any precipitated material. The next stage of purification consisted of anion-exchange chromatography in a HighFlow Q 16/20 column equilibrated with 20 mM ethanolamine pH 10.0. The sample was passed at 5 ml/min and the unbound material was collected and concentrated in Amicon Ultra 4 (Millipore). It was centrifuged at 3800×g for 15 minutes and filtered through AP and 0.45 µm filter to remove any precipitated material. Finally molecular-sieve chromatography was performed in a Superdex SX200 16/60 column equilibrated with 200 mM $NH_4HCO_3$ at 1 ml/min. The protein came out in the elutant due to its tendency to form aggregates. The pure preparation was lyophilised in the same buffer and kept at 4° C. The final yield of the purification was 42.4 mg per liter of culture medium.

Both proteins were found in the insoluble fraction as inclusion bodies but they could not be solubilised in urea. The purification of QM1 and QM2 resulted in proteins with a purity of over 95% and a size of 34.91 and 39.67 kDa, respectively when the SDS-PAGE was carried out in reducing conditions (FIG. 7).

Example 7

Immunological Tests to Demonstrate the Low Ige-Fixing Reactivity of the Hybrid Proteins to a Mixture of Sera from Patients Allergic to D. pteronyssinus A) Immunodetection An initial evaluation of the IgE-binding activities by the QM1 and QM2 chimeras was carried out by the immunotransfer technique using a mixture of sera from patients allergic to D. pteronyssinus. After the protein extracts and the purified proteins were applied to polyacrylamide gels, electrotransfer was carried out using the method of Towbin et al [Towbin, H., Staehelin, I., and Gordon, J. (1979). Electrophoretic transfer of proteins from polyacrylamide gels to nitrocellulose sheets: Procedure and some applications. Proc. Natl. Acad. Sci. USA 76, 4350-4354]. The proteins separated by SDS-PAGE were electrotransferred to PVDF (polyvinylidene difluoride) Hybond-P sheets (GE-Healthcare). After the sheets had been blocked for 1 hour at ambient temperature, they were incubated overnight at 4° C. with a primary antibody and after various washings with the same washing buffer, the sheets were incubated for 1 hour at ambient temperature with a secondary antibody combined with peroxidase. Band detection was carried out using the ECL chemiluminescent method (GE-Healthcare) as mentioned by the manufacturer by exposing the sheet to a film (Hyperfilm.ECL, GE-Healthcare).

The immunodetection tests were not quantitative but showed a different IgE-binding capacity between the two chimeras; thus only in the case of QM1 was there a slight recognition of IgE antibodies, while in the case of the QM2 chimera recognition was zero (FIG. 8).

B) Direct ELISA

IgE reactivity of the two chimeras was analysed by the ELISA technique with individual sera from patients allergic to D. pteronyssinus. The polystyrene plates (Greiner) were incubated overnight at ambient temperature with 0.1 µg per small cup of equimolecular mixture of pure proteins nDer p 1 and nDer p 2 in PBS buffer (10 mM phosphate pH 7.2; 137 mM NaCl 2.7 mM KCl). They were blocked with 200 µl/small cup of PBS supplemented with BSA 1%-Tween 20 0.05% and maintained for 1 hour at 37° C. Next 100 µl/small cup of the mixture of sera from patients allergic to *D. pteronyssinus* was added at dilution 1/4, and left at 37° C. for 90 min. After 3 washings with 200 µl/small cup of PBS-T (PBS+Tween 20 0.05%), 100 µl/small cup of an antiserum against human IgE immunoglobulins (Dako) was added combined with peroxidase (dilution 1:1000) and incubated for 90 minutes at 37° C. After three more washings with PBS-T, 200 µl/small cup of a solution of o-phenylendiamine (Sigma-Fast Tablet Sets, Sigma) prepared according to the instructions of the manufacturer was added and the plates were kept in the dark for 30 minutes. The reaction was stopped with 50 µl/small cup of 3 M $H_2SO_4$ and absorbency was measured at 492 nm in an ELISA Easy Reader EAR-400 AT plate reader (SLT-Lab Instruments).

IgE reactivity to the QM1 chimera was only shown in some patients, whereas QM2 was not recognised by practically any of the IgE antibodies of the patient serum (FIG. 9).

C) ELISA-Inhibition

IgE reactivity to the two chimeras was analysed by the ELISA inhibition technique with a mixture of individual sera from patients allergic to *D. pteronyssinus*. The technique was the same as the previous one except that the mixture of sera from patients allergic to *D. pteronyssinus* was preincubated at a dilution of 1/10 with particular concentrations of inhibitor proteins (from 0.025 to 2500 ng/ml), overnight at 4° C. The IgE-bound antibodies were then detected as for the direct ELISA.

In ELISA inhibition tests, the QM1 chimera showed a lower degree of inhibition than the equivalent mixture of nDer p 1-nDer p 2. Thus the quantity of nDer p 1-nDer p 2 necessary to achieve 50% inhibition was 1 ng/ml, whereas 2500 ng/ml had to be added to achieve the same effect with the QM1 chimera (FIG. 10). This would indicate that QM1 has 2500 times less binding capacity to patients' specific IgEs and its allergencity would therefore be reduced by 99.96%. The QM2 chimera is incapable of binding specific IgEs of patients allergic to *D. pteronyssinus*, and therefore its behaviour in the ELISA inhibition tests did not vary from that obtained with a negative control, such as bovine serum albumin.

Example 8

In Vivo Experiments to Demonstrate the Low Skin Reactivity of the QM1 and QM2 Hybrid Proteins In vivo skin prick tests were carried out on 107 mite-allergic patients to evaluate the hypoallergenicity of the QM1 and QM2 chimeras.

Skin tests were performed with an extract of *D. pteronyssinus*, nDer p 1 and nDer p 2 isolated from mites; rDer p 2 expressed in *E. coli*, and the QM1 and QM2 chimeras. All samples were diluted in 0.5% phenolated and 50% glycerinated physiological saline solution. The concentrations used were 1, 10, and 100 µg/ml for the unmodified purified proteins (nDer p 1, nDer p 2, and rDer p 2) and 5, 50 and 500 µg/ml for the chimeras. NaCl 0.9% and histamine hydrochloride (10 mg/ml) were used as negative and positive controls, respectively.

In the experiment, a drop of each allergen was placed for testing on the inner forearm which was then pricked through the drop with a lancet. Each test was duplicated in rows for comparison of increasing and decreasing concentrations. After 15 min, wheals were circled with a fine point black marker pen. Strips of hypoallergenic sticking plaster were placed on the wheal and pressed gently to transfer the trace of ink onto the strip, which was transferred to the wheal recording sheets. The wheal areas were measured by digitalised entries, using the digitalising writing pad Summasketch and a computer assisted design program (Autocad v. 11).

A correlation was observed between the measured reactivity and the concentration of allergen applied. The QM2 chimera was slightly reactive as reactivity was only observed at the maximum concentration (500 µg/ml) in 5 of the 107 patients studied (4.7%). The QM1 chimera was more reactive, with 86 patients (80.4%) having a positive reaction to 500 µg/ml and 16 (16.8%) having a positive reaction to 50 µg/ml, but with far less reactivity than the wildtype proteins. A statistical study was carried out to interpret the results obtained comparatively by showing the results in box plotting diagrams and using the Wilcoxon test for two related variables (FIG. 10). It can be seen in these illustrations that the distributions of the values for the skin reactions (measured as wheal area in $mm^2$) are significantly different ($P<0.001$) when QM1 at the maximum concentration of 500 µg/ml (median 40.33 $mm^2$, confidence interval 95%: 35.05-47.88) was compared with those for nDer p 1, nDer p 2, and rDer p 2 at 100 µg/ml, reactivity to these being greater than that induced by QM1, with median values of 52.96; 78.86; and 75.72 $mm^2$, respectively.

However, the reactivity of QM1 was not significantly different ($P=0.067$) from that of nDer p 2 at 10 µg/ml (median 41.91 $mm^2$, confidence interval 95%: 28.27-49.71). Nor was it ($P=0.872$) when compared with the reactivity of the complete mite extract (median 39.55 $mm^2$, confidence interval 95%: 34.10-44.40). In this regard it is useful to note that the preparation of mite extract used for the prick diagnosis contained 7.96 and 2.22 µg/ml of Der p 1 and Der p 2, respectively compared with the 500 µg/ml of protein present in QM1.

It can also be seen in these illustrations that the distributions are significantly different for QM2 compared with the mite extract (DPT), nDer p 1, and nDer p 2 ($P<0.001$).

Example 9

Comparative SPT Value of the Chimeras

The allergen concentration values that produced a wheal similar to that produced by histamine at 10 mg/ml were compared. To do this, the method described in the Nordic Guidelines was followed [(24) Registration of allergen preparations. Nordic Guidelines (1989). NLN Publication 23, Uppsala, Sweden]. The protein concentration that produced a wheal similar to that produced by histamine was calculated for each patient from the geometric means of the wheals obtained for each protein at the different concentrations and the average of these values was then calculated for the group of patients studied.

It was observed that the protein concentrations that produced a wheal similar to that produced by histamine were 20.5 and 17.4 µg/ml for nDer p 1 and nDer p 2, respectively, while for the QM1 chimera it was as high as 182.4 µg/ml.

Example 10

Experiments to Demonstrate the Low Ige Antibody-Binding Capacity of the Hybrid Proteins QM1 and QM2

In addition to the in vivo tests, in vitro tests were carried out by determining specific IgE, using the EAST direct technique.

Specific IgE was determined, according to Ceska et al. [(25) Ceska, M. and Lundkvist, U. (1972). A new and simple radioimmunoassay method for the determination of IgE. Immunochemistry 9, 1021-1030], by coupling the natural and recombinant proteins (50 µg/ml) to discs activated with cyanogen bromide, and also extract of *D. pteronyssinus* (500 µg/ml). Next, 50 µl of serum from patients were added and incubated for 1 hour at ambient temperature. After washing, the discs were incubated for 30 minutes at 37° C. with 50 µl of human anti-IgE antibody bound to alkaline phosphatase and quantified following the instructions described by the manufacturer in the protocol of the Hytec specific IgE EIA kit (Hycor Biomedical Inc.).

The results obtained simply reaffirmed those obtained in vivo. The capacity of the QM2 chimera to bind IgE antibodies is very low since only 7 of the 107 sera studied (6.5%) had IgE antibodies capable of binding to QM2. The number of sera with specific IgEs for QM1 was 88 (82.2%). The IgE-binding capacity of QM1 (median 17.01 U/ml, confidence interval 95%: 9.92-27.16) was significantly different (P<0.001) and lower than that of the complete extract (median 39.35 U/ml, confidence interval 95%: 18.80-50.90) (FIG. 11).

Example 11

Experiments to Demonstrate the Basophil-Activation Capacity of the Hybrid Proteins QM1 QM2

The experiments were carried out using the basophil stimulation test measured by flow cytometry (Flow-cytometric cellular allergen stimulation test) performed as described in Sanz et al. [(26) Sanz, M. L., Sanchez, G., Gamboa, P., Vila, L., Uasuf, C., Chazot, M. (2001) Allergen-induced basophil activation: CD63 cell expression detected by flow cytometry in patients allergic to *D. pteronyssinus* and *Lolium perenne*. Clin. Exp. Allergy 31, 1007-1013].

The blood cells situated in the layer above the erythrocytes were collected by centrifugation and resuspended in HEPES-$Ca^{2+}$ buffer (20 mM HEPES, 133 mM NaCl, 5 mM KCl, 7 mM $CaCl_2$, 3.5 mM $MgCl_2$, 1 mg/ml BSA, pH 7.4) containing IL3 (2 ng/ml) and 10 µl of heparine (5000 UI/ml). The allergens and control solutions (50 µl) were added to small cups in polystyrene plates with U-shaped bottoms (Greiner Microlon, Greiner-Bio One, Frickenhausen, Germany) at concentrations that varied between 2 µg/ml and 0.02 pg/ml, mixed with 50 µl of the suspension of cells from patients and incubated at 37° C. for 40 minutes. The reaction was stopped by adding 100 µl of HEPES buffer with no $Ca^{2+}$ or $Mg^{2+}$ but containing 0.27 mM EDTA (washing buffer), and the plates were centrifuged. The basophils of the cell pellet were marked with anti-CD63 antibodies marked with PE (Phycoerythrin) and anti-IgE antibodies marked with FITC (Fluorescein Isothiocyanate) (dilutions 1:80 and 1:60, respectively, Caltag, Burlingame, USA) and incubated for 30 minutes at 4° C., subsequently 4 ml of erythrolytic reagent were added (Ortho Diagnostic System, Madrid, Spain). Cellular lysis was stopped by adding washing buffer and after centrifuging the cells, the supernatants were diluted with 500 µl of the same buffer. The surface markers of the basophils were analysed by flow cytometry at 488 nm using a FACScan flow cytometry appliance equipped with a 15 nW argon laser (Becton Dickinson, San Jose, USA) and the data were analysed using the CellQuest computer package. In each test the anti-IgE and anti-CD63 marking was studied in at least 500 basophils.

The monoclonal anti-IgE antibody, Le27 (1 µl/ml; Bühlmann, Allschwil, Switzerland) was used as a positive control and the basal values without stimulation were evaluated with HEPES-$Ca^{2+}$ buffer. The activation responses were considered positive when the stimulation index (% basophils activated with *D. pteronyssinus* extract or purified protein/% basophils activated in basal conditions) was ≥2 at any of the concentrations of *D. pteronyssinus* extract or purified protein used, and the specific activation due to the allergen was >10%.

None of the control subjects showed a positive result for either of the chimeras QM1 or QM2. Of the 33 patients allergic to *D. pteronyssinus* studied, QM1 gave a positive response in 28, whereas with QM2 there was a positive response in only 10 cases and always at much lower concentrations than those at which QM1 gave a positive response.

Example 12

Induced Lymphoproliferation Experiments to Demonstrate the Immunogenic Capacity of the Hybrid Proteins QM1 and QM2

An essential requirement for the use of a hypoallergenic molecule in immunotherapy is that antigenicity thereof (T epitopes) be maintained. Therefore to check whether as well as not binding IgE antibodies, the hybrid proteins continued to be antigenic, a lymphoproliferation study was carried out on peripheral blood mononuclear cells (PBMC) stimulated by the different proteins used in the experiments. They were carried out by incorporation of a fluorescein derivative in cultures of purified lymphocytes. This derivative (carboxyfluorescein succinimidyl ester (CFSE)) could pass through the cellular membrane but was not fluorescent until it had been degraded by the cellular esterases being converted into a fluorescent compound incapable of passing through the cellular membrane. CFSE incorporation was analysed by flow cytometry in a BD FACSCalibur flow cytometer (Becton-Dickinson, Franklin Lakes N.J., USA).

PBMCs of 23 patients allergic to *D. pteronyssinus* were isolated by density gradient centrifugation using a lymphocyte separation solution (Lymphoprep, Nycomed). The PBMCs were then resuspended at $1-2 \times 10^6$ viable cells/ml in culture medium (RPMI 1640, Sigma Chemical Co.) and the viability thereof was tested with 0.25% of trypan blue in PBS (Sigma Chemical Co.). The prepared PBMCs with viability above 90% were used immediately for the in vitro proliferation tests. $10 \times 10^6$ PBMCs in RPMI-1640 were marked with CFSE (final concentration 5 µM) for 10 min at 37° C. and in a humidified atmosphere of 5% $CO_2$. Marking was stopped with 50% foetal calf serum for 5 min and they were washed twice with RPMI-1640 supplemented with 10% foetal calf serum and resuspended at $1-2 \times 10^6$ cells/ml in Complete Medium (RPMI-1640, 50 µg/ml of gentamicin, and glutamine 2 mM) supplemented with 5% human AB serum. They were placed in flat-bottomed microplates with 24 small cups (Nunclon, NUNC), $1-2 \times 10^6$ cells in a final volume of medium of 1 ml and the antigens (extract of *D. pteronyssinus* and the different purified proteins) were added at a final concentration of 10 µg/ml and incubated for 7 days at 37° C. and in a humidified atmosphere of 5% $CO_2$. Analysis by flow cytometry was carried out in a BD FACSCalibur flow cytometer (Becton-Dickinson) with four-colour fluorescence capacity. The results were expressed as a percentage of the events recorded evaluated by the Cell Quest Software program package (Becton-Dickinson). Triplicate controls of non-stimulated cultures were included in all cases. The proteins used in the test were the two hybrid proteins (QM1 and QM2), two equimolecular mixtures of the purified proteins nDer p 1 and nDer p 2 of *D. pteronyssinus* (natural mixture)

and of the recombinant proteins rDer p 1 and rDer p 2 isolated from *E. coli* (recombinant mixture). The extract of *D. pteronyssinus* was also used as a control.

In the first step a sweep of immunogen protein concentrations was carried out to determine the optimum concentration for the subsequent carrying out of the test. In all cases it was observed that the protein concentration that showed the maximum proliferation (IE %) was 10 µg/ml.

The proliferation results with the 23 patients allergic to *D. pteronyssinus* were analysed by statistical box plotting diagram analysis and non-parametric tests for the two matched samples. It could be seen from the statistical analysis that the extract of *D. pteronyssinus* (average 12%, confidence interval 95%: 8-20), used as a control, had an antigenic stimulation capacity not significantly different from that of the chimeras QM1 (average 15%, confidence interval 95%: 10-25) and QM2 (average 13%, confidence interval 95%: 8-17) (P=0.121 and P=0.304, respectively). However, the immunogenicity of QM1 was significantly higher (P<0.05) than that obtained with the natural mixture (average 9%, confidence interval 95%: 5-13) or the recombinant mixture (P<0.005) (average 9%, confidence interval 95%: 57-14.5). When the two chimeras were compared with each other, it was observed that the capacity to induce immunoproliferation was significantly greater in the case of QM1 (P<0.005) (FIG. 13).

From the results obtained it could be seen that both QM1 and QM2 continued to maintain immunoproliferation induction capacity and this was even greater in the fused proteins compared with the wildtype proteins.

Example 13

QM1 and QM2 Induced Antibodies Inhibit Patients' IgE Binding to Natural Allergens For this purpose immunization of mice with the hybrids were performed. Six-week-old female BALB/c mice (Haarlam, Barcelona, Spain) were immunized intraperitoneally, five times each fifteen days, with 10 µg of either the equimolar mix of purified nDer p 1 and nDer p 2 (nD1D2), QM1 or QM2 adsorbed to aluminium hydroxide. Six mice were used for each protein and sera were obtained 10 days after the last boost via bleeding from the submandibular vein, pooled and stored at −20° C. until use.

Firstly, it was checked whether the antisera raised by immunization of mice with nD1D2, QM1, and QM2 were reactive to nD1D2 using ELISA titration experiments. The ELISA experiments were performed as described in Example 7B, but two-fold dilutions of the mice antisera were added and then wells were incubated with horseradish peroxidase-conjugated mouse anti-mouse IgG antibody (Sigma Chemical, St. Louis, Mo., USA) diluted 1/2000. After three washes, the peroxidase activity was measured adding 200 µL/well of a solution of o-phenylendiamine (Sigma). After 30 min, colour reaction was stopped by adding 50 µl/well of 3 M $H_2SO_4$, and the optical density was read at 492 nm.

Antisera raised by immunization of mice with an equimolar mix of purified nDer p 1 and nDer p 2 (nD1D2), QM1, and QM2 reacted to nD1D2, showing that immunization with both hybrids lead to higher nD1D2-specific IgG antibody levels compared to immunization with nD1D2 (FIG. 14A).

In order to investigate whether mice IgG against hybrid molecules could inhibit binding of patient serum IgE to nD1D2, a competitive ELISA was performed with individual sera from nine house dust mite (HDM)-allergic patients or a pool of sera (diluted 1/50) from 30 HDM-allergic patients. ELISA plates (Greiner) were coated (100 ng/well) overnight with nD1D2 in PBS, preincubated with a 1/20 dilution of anti-nD1D2, anti-QM1, and anti-QM2 serum pools of 6 mice. A preimmune serum pool was used as immunization control. After washing, plates were incubated with individual sera (diluted 1/20 and 1/50) or a pool of sera (diluted 1/50) from HDM-allergic patients. Bound IgE antibodies were detected with a Horseradish Peroxidase (HRP)-labelled anti-human IgE mAb (Southern, Birmingham, Ala.) diluted 1/2000 and o-phenylendiamine (Sigma). The blocking capacity was expressed as a percentage signal of wells with no mouse serum added.

Specific mouse antibodies raised by hybrid proteins immunization were able to block the binding of nine mite-allergic patients' IgE to the equimolar mix of purified nDer p 1 and nDer p 2 (nD1D2) in a different way. The inhibition obtained with mouse anti-nD1D2 antibodies was between 41 and 72% (mean 56%) while mouse anti-QM1 and anti-QM2 antibodies inhibited serum IgE-binding to nD1D2 between 43 and 82% (mean 60%) and between 0 and 45% (mean 20%), respectively (Table I). The inhibition obtained with mouse anti-nD1D2 antibodies was slightly lower (although not statistically different; P=0.139) than that obtained with mouse anti-QM1 antibodies. The inhibition obtained in mouse anti-QM2 group was statistically different (P<0.01) to those obtained in anti-nD1D2 and anti-QM1 groups.

TABLE I

Percent inhibition of patients' IgE binding to nD1D2 by nD1D2-, QM1-, and QM2-specific mouse IgG antibodies.

| Patient | anti-nD1D2 | anti-QM1 | anti-QM2 |
|---|---|---|---|
| #6 | 51% | 56% | 0% |
| #28 | 52% | 57% | 19% |
| #34 | 69% | 77% | 36% |
| #38 | 41% | 49% | 11% |
| #41 | 41% | 43% | 24% |
| #49 | 64% | 53% | 21% |
| #50 | 60% | 57% | 9% |
| #100 | 54% | 65% | 18% |
| #104 | 72% | 82% | 45% |
| Mean | 56% | 60%[§] | 20%* |

[§]Not statistically significant difference with anti-nD1D2 group (P = 0.139).
*Statistically significant differences (P < 0.01) with anti-nD1D2 and and-QM1 groups.

Additionally, the mouse blocking antisera were evaluated using a pool of sera from 30 HDM-allergic patients (FIG. 14B). Mouse IgG raised against QM1 and QM2 inhibited serum IgE binding to nD1D2 by 71% and 26%, respectively, whereas the inhibition obtained with mouse anti-nD1D2 antibodies or pre-immune sera was 65% and 17%, respectively (FIG. 6B). The partial inhibition of IgE reactivity by QM2-induced IgG was due to the very low inhibition of specific IgE to Der p 2. The ability of anti-QM2 IgG antibodies to interfere with patients' IgE binding to Der p 2 was much lower than that of anti-QM1 sera (13 and 85%, respectively). On the contrary, the inhibition of IgE-binding to Der p 1 was comparable in both mouse antisera (inhibition with anti-QM2: 52%; with anti-QM1: 52%) (FIG. 14B).

IgE-binding from HDM-allergic patient sera to nD1D2 was inhibited by IgG induced with each hybrid although QM1-induced IgG showed a better inhibitory capacity compared with IgG-induced with QM2.

Such only partial inhibition of IgE reactivity as seen with QM2-induced antiserum has been also found with a Phl p 2-mosaic [(30) Mothes-Luksch, N., Stumvoll, S., Linhart, B., Focke, M., Krant, M-T., Hanswirth, A., Valent, P., Verdino, P., Keller, W., Grote, M., Valenta, R. (2008). Disruption of allergenic activity of the major grass pollen allergen Phl p 2 by reassembly as mosaic protein. J Immunol 181, 4864-4873].

There, authors suggested that it could due to the destruction of IgE epitopes and thus no IgG could be induced against the original IgE epitopes. This could be the case on QM2 since IgG-blocking activity of IgE binding to Der p 2 is very low and the IgE-reactivity of this hybrid was almost abolished.

The low ability of mouse anti-nD1D2 antibodies to inhibit IgE binding to itself (60-65%; Table I and FIG. 14B) was similar to that reported in the case of Der p 2 specific IgE [Chen, K.-W., Fuchs, G., Sonneck, K., Gieras, A., Swoboda, I., Douladiris, N., Linhart, B., Jankovic, M., Pavkov, T., Keller, W., Papadopoulos, N. G., Valent, P., Valenta, R., Vrtala, S. (2008). Reduction of the in vivo allergenicity of Der p 2, the major house-dust mite, by genetic engineering. Mol. Immunol. 45, 2486-2498]. These differences between the specificity of murine IgG and human IgE responses to mite allergens could be influenced in part by the different mode of immunization as has been reported before by Chapman et al. (1987). [Chapman, M. D., Heymann, P. W., Platts-Mills, T. A. E. (1987). Epitope mapping of two major inhalant allergens, Der p 1 and Der p 2, from mites of the genus *Dermatophagoides*. J. Immunol. 139, 1479-1484]. In mice, which are immunized by IP injections containing adjuvants, antigens are extensively processed while in humans, which are sensitized by inhalation of minute quantities of allergen without adjuvants, either limited allergen processing or a different form of processing occurs. Both QM1 and QM2 exhibited higher T-cell stimulating capacity and induced stronger protective antibody responses than the separated molecules.

From the above, it can be concluded that the hybrid proteins QM1 and QM2 are two hypoallergenic molecules to develop satisfactory immunotherapy against allergy to *D. pteronyssinus*.

ADMINISTRATION METHODS

The present invention covers the use of the hypoallergenic chimeras described above or synthetic peptides derived therefrom for hyposensitisation treatments in mammals. The hyposensitisation method involves the repeated administration by parenteral (subcutaneous, intravenous or intramuscular), inhalation, oral, sublingual, nasal or rectal routes of the allergen in question. The chimeras may be administered alone or in combination with other pharmacologically acceptable diluents and excipients, according to current legislation and the applicable galenic procedures.

The invention claimed is:

1. A chimeric polypeptide comprising SEQ ID No:2 or SEQ ID No:4.

2. A method for treatment of an allergic reaction to mite allergen, comprising administering to a patient suffering from said reaction, a therapeutically effective amount of the chimeric polypeptide of claim 1.

3. A pharmaceutical formulation comprising the chimeric polypeptide of claim 1 in combination with a pharmaceutically acceptable excipient.

4. A method for treatment of an allergic reaction to mite allergen comprising administering to a patient suffering from said allergic reaction, a pharmaceutical formulation of claim 3.

5. The pharmaceutical formulation of claim 3, formulated in the form of a solution, suspension, emulsion, lyophilizate, laminate, or transdermal patch.

6. A pharmaceutical formulation of claim 3 compounded for subcutaneous, sublingual, oral, nasal, rectal, topical, inhalation, or parenteral administration.

7. The chimeric polypeptide of claim 1, wherein the sequence is SEQ ID No:2.

8. The chimeric polypeptide of claim 1, wherein the sequence is SEQ ID No:4.

* * * * *